(12) United States Patent
Manabe et al.

(10) Patent No.: US 9,416,231 B2
(45) Date of Patent: Aug. 16, 2016

(54) POLYHEDRAL POLYSILOXANE MODIFIED PRODUCT AND COMPOSITION USING THE MODIFIED PRODUCT

(71) Applicant: KANEKA CORPORATION, Osaka (JP)

(72) Inventors: Takao Manabe, Osaka (JP); Makoto Seino, Osaka (JP); Shinya Mizuta, Osaka (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 14/689,454

(22) Filed: Apr. 17, 2015

(65) Prior Publication Data

US 2015/0218319 A1    Aug. 6, 2015

Related U.S. Application Data

(62) Division of application No. 13/770,089, filed on Feb. 19, 2013, now Pat. No. 9,035,009, which is a division of application No. 12/450,905, filed as application No. PCT/JP2008/057415 on Apr. 16, 2008, now Pat. No. 8,399,592.

(30) Foreign Application Priority Data

| | | |
|---|---|---|
| Apr. 17, 2007 | (JP) | 2007-108583 |
| May 21, 2007 | (JP) | 2007-134431 |
| Dec. 27, 2007 | (JP) | 2007-336850 |
| Jan. 23, 2008 | (JP) | 2008-013179 |
| Jan. 23, 2008 | (JP) | 2008-013180 |
| Jan. 23, 2008 | (JP) | 2008-013182 |
| Jan. 23, 2008 | (JP) | 2008-013183 |
| Jan. 23, 2008 | (JP) | 2008-013184 |
| Jan. 23, 2008 | (JP) | 2008-013185 |
| Jan. 23, 2008 | (JP) | 2008-013198 |

(51) Int. Cl.

| | |
|---|---|
| *C08L 83/04* | (2006.01) |
| *C08G 77/38* | (2006.01) |
| *C08F 230/08* | (2006.01) |
| *C07F 7/21* | (2006.01) |
| *C08G 77/04* | (2006.01) |
| *C08G 77/14* | (2006.01) |
| *C08G 77/20* | (2006.01) |
| *C08G 77/50* | (2006.01) |
| *C09D 183/04* | (2006.01) |
| *C08K 3/36* | (2006.01) |
| *G02B 1/04* | (2006.01) |
| *G02B 1/10* | (2015.01) |
| *C08G 77/12* | (2006.01) |
| *C08K 5/56* | (2006.01) |

(52) U.S. Cl.
CPC . *C08G 77/38* (2013.01); *C07F 7/21* (2013.01); *C08F 230/08* (2013.01); *C08G 77/04* (2013.01); *C08G 77/045* (2013.01); *C08G 77/14* (2013.01); *C08G 77/20* (2013.01); *C08G 77/50* (2013.01); *C08K 3/36* (2013.01); *C09D 183/04* (2013.01); *G02B 1/04* (2013.01); *G02B 1/10* (2013.01); *C08G 77/12* (2013.01); *C08K 5/56* (2013.01)

(58) Field of Classification Search
CPC ................................ C08G 77/12; C08G 77/20
See application file for complete search history.

(56) References Cited

U.S. PATENT DOCUMENTS

| | | | |
|---|---|---|---|
| 4,618,657 | A | 10/1986 | Katchko et al. |
| 5,047,492 | A | 9/1991 | Weidner et al. |
| 5,160,787 | A | 11/1992 | Gaku et al. |
| 5,939,576 | A | 8/1999 | Lichtenhan et al. |
| 6,127,503 | A | 10/2000 | Fujioka et al. |
| 6,252,030 | B1 | 6/2001 | Zank et al. |
| 6,623,711 | B2 | 9/2003 | Lyu et al. |
| 8,299,198 | B2 | 10/2012 | Manabe et al. |
| 8,399,592 | B2 | 3/2013 | Manabe et al. |
| 2003/0105246 | A1 | 6/2003 | Andoh et al. |
| 2004/0116566 | A1 | 6/2004 | Fehn |
| 2005/0173780 | A1 | 8/2005 | Sethumadhavan et al. |

(Continued)

FOREIGN PATENT DOCUMENTS

| | | |
|---|---|---|
| CN | 101548398 | 9/2009 |
| CN | 101568546 | 10/2009 |

(Continued)

OTHER PUBLICATIONS

Michelle Velderrain, "Moisture Permeability of Silicone Systems, Case Study #1, Water Vapor Transmission Rate as Influenced by Durometer, Silica, and Organic-Siloxane Group", NuSil Technology Technical Publication, Jun. 24, 2009.

(Continued)

*Primary Examiner* — Kuo-Liang Peng
(74) *Attorney, Agent, or Firm* — Wenderoth, Lind & Ponack, L.L.P.

(57) ABSTRACT

The present invention has its object to provide a liquid-form modified product of polyhedral polysiloxane which is excellent in moldability and transparency, and a composition produced using the modified product. In addition, the present invention can provide an easy-to-handle modified product and composition. The present invention provides a modified product of polyhedral polysiloxane which is obtainable by modifying a polyhedral polysiloxane compound (a) with a compound (b), and a composition containing the modified product. The polyhedral polysiloxane compound (a) has an alkenyl group and/or a hydrosilyl group, and the compound (b) has a hydrosilyl group and/or an alkenyl group each capable of hydrosilylation with the component (a).

30 Claims, No Drawings

(56) References Cited

U.S. PATENT DOCUMENTS

| | | | |
|---|---|---|---|
| 2006/0052623 A1 | 3/2006 | Yoshida et al. | |
| 2006/0074213 A1* | 4/2006 | Kiyomori | C07F 7/21 528/31 |
| 2006/0122351 A1 | 6/2006 | Laine et al. | |
| 2007/0045619 A1 | 3/2007 | Park et al. | |
| 2007/0088094 A1 | 4/2007 | Tamaki et al. | |
| 2008/0020213 A1 | 1/2008 | Lichtenhan et al. | |
| 2008/0090986 A1 | 4/2008 | Khanarian et al. | |
| 2009/0225640 A1 | 9/2009 | Manabe et al. | |
| 2010/0063221 A1 | 3/2010 | Manabe et al. | |
| 2010/0099790 A1 | 4/2010 | Manabe et al. | |
| 2011/0001190 A1 | 1/2011 | Ide et al. | |
| 2011/0251357 A1 | 10/2011 | Laine et al. | |
| 2013/0131264 A1 | 5/2013 | Nishimiya et al. | |

FOREIGN PATENT DOCUMENTS

| | | |
|---|---|---|
| EP | 0 348 705 | 1/1990 |
| EP | 2151443 | 2/2010 |
| JP | H02-67290 | 3/1990 |
| JP | 6-329687 | 11/1994 |
| JP | 11-71462 | 3/1999 |
| JP | 11-124502 | 5/1999 |
| JP | 2000-154252 | 6/2000 |
| JP | 2000-265066 | 9/2000 |
| JP | 2002-363414 | 12/2002 |
| JP | 2003-137944 | 5/2003 |
| JP | 2004-123936 | 4/2004 |
| JP | 2004-143449 | 5/2004 |
| JP | 2004-175887 | 6/2004 |
| JP | 2004-529984 | 9/2004 |
| JP | 2004-359933 | 12/2004 |
| JP | 2005-23256 | 1/2005 |
| JP | 2005-290352 | 10/2005 |
| JP | 2006-022207 | 1/2006 |
| JP | 2006-104325 | 4/2006 |
| JP | 2006-131850 | 5/2006 |
| JP | 2006-233155 | 9/2006 |
| JP | 2006-265514 | 10/2006 |
| JP | 2006-269402 | 10/2006 |
| JP | 2006-299149 | 11/2006 |
| JP | 2006-299150 | 11/2006 |
| JP | 2007-031619 | 2/2007 |
| JP | 2007-31619 | 2/2007 |
| JP | 2007-091935 | 4/2007 |
| JP | 2007-169427 | 7/2007 |
| JP | 2008-163260 | 7/2008 |
| JP | 2009-173759 | 8/2009 |
| JP | 2009-173789 | 8/2009 |
| JP | 2009-206124 | 9/2009 |
| JP | 2010-031254 | 2/2010 |
| JP | 2010-095616 | 4/2010 |
| JP | 2010-254927 | 11/2010 |
| JP | 2010-265410 | 11/2010 |
| JP | 2011-006546 | 1/2011 |
| JP | 2011-016968 | 1/2011 |
| JP | 2011-042732 | 3/2011 |
| JP | 2011-068753 | 4/2011 |
| JP | 2012-180513 | 9/2012 |
| WO | 03/042292 | 5/2003 |
| WO | 2004/011525 | 2/2004 |
| WO | 2004/022231 | 3/2004 |
| WO | 2004/024741 | 3/2004 |
| WO | 2006/062219 | 6/2006 |
| WO | 2007/022367 | 2/2007 |
| WO | 2008-010545 | 1/2008 |
| WO | 2008/063884 | 5/2008 |
| WO | 2008/066116 | 6/2008 |
| WO | 2008/133138 | 11/2008 |
| WO | 2011-148896 | 12/2011 |

OTHER PUBLICATIONS

Michelle Velderrain, "Designing low permeability, optical-grade silicone systems-Guidelines for choosing a silicone based on transmission rates for barrier applications", NuSil Technology Technical Publications, Jan. 26, 2012.

Translation of International Preliminary Report on Patentability (Form PCT/IB/373) of International Application No. PCT/JP2011/070854 issued Apr. 16, 2013.

Valderrain et al., "Moisture Permeability of Silicone Systems, Case Study #2", NuSil Silicone Technology, Mar. 4, 2011.

Zhang et al., "The Permeability Characteristics of Silicone Rubber", SAMPE Fall Technical Conference, Nov. 6-9, 2006.

Li et al. (Polyhedral Oligomeric Silsesquioxanes (POSS) Polymers and Copolymers: A Review, Journal of Inorganic and Organometallic Polymers, 11(3), 123-154, Sep. 2001).

Translation of Notification of Transmittal of Translation of the International Preliminary Report on Patentability (Form PCT/IB338) of International Application No. PCT/JP2007/064233 mailed Feb. 5, 2009 with forms PCT/IB/373 and PCT/ISA/237.

C. Zhang et al., "Highly Porous Polyhedral Silsesquioxane Polymers. Synthesis and Characterization", J. Am. Chem. Soc., vol. 120, pp. 8380-8391, 1998.

R. M. Laine et al., "Polyfunctional Cubic Silsesquioxanes as Building Blocks for Organic/Inorganic Hybrids", Applied Organometallic Chemistry, vol. 12, pp. 715-723, 1998.

A. Sellinger et al., "Silsesquioxanes as Synthetic Platforms. Thermally Curable and Photocurable Inorganic/Organic Hybrids", Macromolecules, vol. 29, pp. 2327-2330, 1996.

International Preliminary Report on Patentability (Form PCT/IB/373) of International Application No. PCT/JP2011/061757 mailed Dec. 4, 2012 with Form PCT/ISA/273, English translation only.

International Search Report of PCT/JP2007/064233 mailed Oct. 9, 2007.

International Search Report of PCT/JP2011/061757 mailed Sep. 6, 2011.

International Preliminary Report on Patentability (Form PCT/IB/373) of International Application No. PCT/JP2008/057415 issued Nov. 10, 2009 with Form PCT/ISA/273, English translation only.

Jaffres, Paul-Alain et al., "Synthesis of highly functionalized dendrimers based on polyhedral silsesquioxane cores", J. Chem. Soc, Dalton Trans., pp. 2767-2770, Feb. 23, 1988.

Lin et al., "Chapter 18: LED and Optical Device Packaging and Materials," Materials for Advanced Packaging (2009), pp. 629-680.

McCan, Softening of Octyl-modified Phenylsilsesquioxane, Polimeri, 32(2011) 3-4:112-118.

English translation of International Preliminary Report on Patentability.

Bill Riegler, et al., "NuSil Silicone Technology, Phosphors and Silicone Dispersions," Presented at Phosphor Global Summit, Feb. 28 to Mar. 2, 2005, 19 pages.

* cited by examiner

POLYHEDRAL POLYSILOXANE MODIFIED PRODUCT AND COMPOSITION USING THE MODIFIED PRODUCT

TECHNICAL FIELD

The present invention relates to a modified product, particularly in liquid form, of polyhedral polysiloxane which is excellent in moldability, transparency, and heat and light resistances. The present invention also relates to a composition comprising the modified product.

BACKGROUND ART

Polysiloxane compositions are excellent in heat resistance, cold resistance, weather resistance, light resistance, chemical stability, electrical characteristics, flame retardancy, water resistance, transparency, colorability, anti-stick properties, and anti-corrosion properties, and thus have been utilized in various industrial fields. In particular, it is known that polyhedral polysiloxanes are more excellent in various properties such as heat resistance, light resistance, chemical stability, and low dielectricity owing to their unique chemical structure. On the other hand, a polyhedral polysiloxane is generally a polyfunctional solid compound, and thereby the polyhedral polysiloxane has poor handleability and moldability and it is difficult to control the reaction of the polyhedral polysiloxane. Thus, it is difficult to provide a molded product from the polyhedral polysiloxane.

For example, Non-Patent Document 1 discloses a hydrosilylated curable composition produced using a functional group-containing polyhedral polysiloxane. In this disclosure, the polyhedral polysiloxane as a starting material is a polyfunctional solid and thereby it is difficult to control a curing reaction of the polysiloxane, leading to difficulties in coating and injection molding.

As polyhedral polysiloxane compounds, various compounds with different functional groups have been known, such as an epoxy group-containing compound (Patent Document 1), a (meth)acryloyl group-containing compound (Patent Document 2), a hydrolyzable silyl group-containing compound (Patent Document 3), and an oxetanyl group-containing compound (Patent Document 4). These compounds are allowed to be cross-linked by heat or light in the presence of curing initiators to provide cured products.

In addition, there have been disclosed curable compositions produced using polyhedral polysiloxanes containing a group such as an epoxy group or a phenyl group (Patent Documents 1, 5, and 6). Such curable compositions cannot sufficiently benefit from properties of polysiloxane compositions; for example, staining occurs on the compositions upon heating at high temperatures.

It can be envisaged that one primary application of these compounds is for various resists. In such a case, the compounds are required to be developable. Nowadays, alkali development is generally employed as a primary developing method, and resists are required to have alkali solubility. The aforementioned compounds are, however, insoluble to alkali, and thus it is required to impart alkali solubility to the compounds.

For imparting alkali solubility, for example, introduction of an organic acid group such as a carboxylate group or a sulfonate group has been known. The introduction of these groups may problematically cause decrease in heat and light resistances that polyhedral polysiloxanes originally have. In other words, what has been required is a technique for imparting alkali solubility without decrease in heat and light resistances.

Materials prepared using polyhedral polysiloxane compounds are disclosed as mentioned above, but there is no disclosure of liquid compounds having properties of siloxane compositions, and also having excellent handleability and moldability. It has been desired to develop a new material.

Patent Document 1: Japanese Kokai Publication 2004-359933
Patent Document 2: Japanese Kokai Publication 2004-143449
Patent Document 3: Japanese Kokai Publication 2006-269402
Patent Document 4: Japanese Kokai Publication 2005-23256
Patent Document 5: Japanese Kohyo Publication 2004-529984
Patent Document 6: Japanese Kokai Publication 2006-22207
Non-Patent Document 1: J. Am. Chem. Soc. 1998, 120, 8380-8391

SUMMARY OF THE INVENTION

An object of the present invention is to provide a modified product of polyhedral polysiloxane, which is excellent in moldability, transparency, heat resistance, light resistance, and adhesiveness, a composition produced using the modified product, and a cured product, for solving the aforementioned problems.

The present inventors have made eager studies to solve the aforementioned problems, which results in completion of the present invention. The present invention has features as follows.

1). A modified polyhedral polysiloxane which is obtainable by modifying a polyhedral polysiloxane compound (a) with a compound (b), wherein the polyhedral polysiloxane compound (a) has an alkenyl group and/or a hydrosilyl group, and the compound (b) has a hydrosilyl group and/or an alkenyl group each capable of hydrosilylation with the component (a).

2). The modified polyhedral polysiloxane according to 1), wherein the modified polyhedral polysiloxane is in a liquid state at 20° C.

3). The modified polyhedral polysiloxane according to 1) or 2), wherein the compound (b) is a cyclic siloxane having a hydrosilyl group and/or an alkenyl group.

4). The modified polyhedral polysiloxane according to 1) or 2), wherein the compound (b) is a linear siloxane having an alkenyl group and/or a hydrosilyl group at a molecular end.

5). The modified polyhedral polysiloxane according to any one of 1) to 4), wherein a molecule of the modified polyhedral polysiloxane contains at least three hydrosilyl groups or alkenyl groups.

6). The modified polyhedral polysiloxane according to any one of 1) to 5), wherein the compound (b) has an alkenyl group and/or a hydrosilyl group, and further has a reactive functional group other than an alkenyl group and a hydrosilyl group.

7). The modified polyhedral polysiloxane according to anyone of 1) to 6), which is obtainable by: adding the compound (b) having a hydrosilyl group and/or an alkenyl group to the polyhedral polysiloxane compound (a) having an alkenyl group and/or a hydrosilyl group to allow the compound (a) to be modified by the compound (b), wherein the number of a hydrogen atom directly bonded to a Si atom and/or an alkenyl group of the compound (b) is 2.5 to 20 per an alkenyl group and/or a hydrogen atom directly bonded to a Si atom of the compound (a); and distilling off an unreacted portion of the compound (b).

8). A modified polyhedral polysiloxane, comprising a siloxane unit represented by the formula:

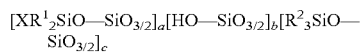

$[XR^1_2SiO\text{—}SiO_{3/2}]_a[HO\text{—}SiO_{3/2}]_b[R^2_3SiO\text{—}SiO_{3/2}]_c$ wherein a+b+c is an integer of 6 to 24, a is an integer of 1 or more, and b and c are each 0 or an integer of 1 or more; X is a reactive functional group-containing group; $R^1$ is an alkyl group or an aryl group; and $R^2$ is an alkyl group, an aryl group, an alkenyl group, a hydrogen atom, or a group bonded to another polyhedral polysiloxane.

9). The modified polyhedral polysiloxane according to 8), wherein b is an integer of 1 or more.

10). The modified polyhedral polysiloxane according to 8) or 9), wherein the reactive functional group-containing group X has at least one functional group selected from the group consisting of an epoxy group, a hydrolyzable silyl group, an oxetanyl group, a (meth)acryloyl group, and a thiol group.

11). The modified polyhedral polysiloxane according to 10), wherein the reactive functional group-containing group X has at least one functional group selected from the group consisting of an epoxy group, a hydrolyzable silyl group, and an oxetanyl group.

12). The modified polyhedral polysiloxane according to 10) or 11), wherein the hydrolyzable silyl group is an alkoxysilyl group.

13). The modified polyhedral polysiloxane according to anyone of 10) to 12), wherein the group having the hydrolyzable silyl group is an alkoxysilylethyl group.

14). The modified polyhedral polysiloxane according to any one of 1) to 13), wherein the modified polyhedral polysiloxane is soluble in an alkaline aqueous solution.

15). The modified polyhedral polysiloxane according to anyone of 9) to 14), which is produced by a process comprising the steps of: synthesizing a polyhedral polysiloxane intermediate containing a siloxane unit having a dialkylsilyl group represented by the formula:

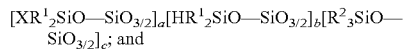

$[XR^1_2SiO\text{—}SiO_{3/2}]_a[HR^1_2SiO\text{—}SiO_{3/2}]_b[R^2_3SiO\text{—}SiO_{3/2}]_c$; and treating the intermediate prepared in the above step with a polar solvent to eliminate the dialkylsilyl group, which results in generation of a silanol group.

16). The modified polyhedral polysiloxane according to 8), wherein at least one X contains a constitutional unit represented by the formula (1) or (2):

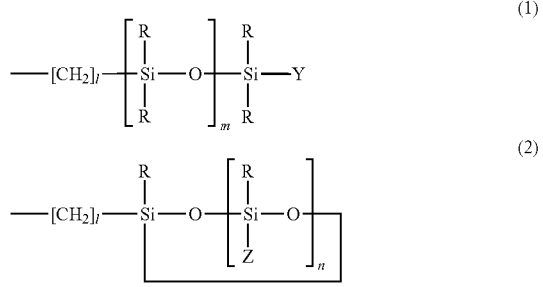

wherein l is an integer of 2 or more; m is an integer of 0 or more; n is an integer of 2 or more; Y is a hydrogen atom, an alkenyl group, an alkyl group, an aryl group, or a moiety bonded to a polyhedral polysiloxane via an alkylene chain, and the Ys may be the same as or different from each other; Z is a hydrogen atom, an alkenyl group, an alkyl group, an aryl group, or a moiety bonded to a polyhedral polysiloxane via an alkylene chain, and the Zs may be the same as or different from each other, provided that at least one of the Ys and Zs is a hydrogen atom or an alkenyl group; and R is an alkyl group or an aryl group, wherein in the case where there are a plurality of Xs, the structures of the formula (1) or (2) may be different from each other, or the structures of the formulas (1) and (2) may coexist.

17). The modified polyhedral polysiloxane according to anyone of 1) to 16), which is obtainable by: adding an excessive amount of the hydrosilyl group-containing compound (b) to the polyhedral polysiloxane compound (a) to allow the compound (a) to be modified with the compound (b) by a hydrosilylation reaction, wherein the number of a hydrogen atom directly bonded to a Si atom is 2.5 to 20 per one alkenyl group; and distilling off an unreacted portion of the hydrosilyl group-containing compound (b), the polyhedral polysiloxane compound (a) containing a siloxane unit represented by the formula:

$[AR^1_2SiO\text{—}SiO_{3/2}]_a[R^4_3SiO\text{—}SiO_{3/2}]_b$ wherein a+b is an integer of 6 to 24, a is an integer of 1 or more, and b is 0 or an integer of 1 or more; As are alkenyl group(s) and/or hydrogen atom(s), provided that at least one of the As is an alkenyl group; $R^1$ is an alkyl group or an aryl group; and $R^4$ is a substituent group other than an alkenyl group and a hydrogen atom, such as an alkyl group, an aryl group, or a group bonded to another polyhedral polysiloxane or siloxane compound.

18). The modified polyhedral polysiloxane according to anyone of 1) to 16), which is obtainable by: adding an excessive amount of the alkenyl group-containing compound (b) to the polyhedral polysiloxane compound (a) to allow the compound (a) to be modified with the compound (b) by a hydrosilylation reaction, wherein the number of an alkenyl group is 2.5 to 20 per one hydrogen atom directly bonded to a Si atom; and distilling off an unreacted portion of the alkenyl group-containing compound (b), the polyhedral polysiloxane compound (a) containing a siloxane unit represented by the formula:

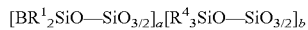

$[BR^1_2SiO\text{—}SiO_{3/2}]_a[R^4_3SiO\text{—}SiO_{3/2}]_b$ wherein a+b is an integer of 6 to 24, a is an integer of 1 or more, and b is 0 or an integer of 1 or more; Bs are alkenyl group(s) and/or hydrogen atom(s), provided that at least one of the Bs is a hydrogen atom; $R^1$ is an alkyl group or an aryl group; and $R^4$ is a substituent group other than an alkenyl group and a hydrogen atom, such as an alkyl group, an aryl group, or a group bonded to another polyhedral polysiloxane or siloxane compound.

19). A modified polyhedral polysiloxane, represented by the formula:

$[XSiO_{3/2}]_a[R^1(WO)SiO]_b[R^2SiO_{3/2}]_c[R^2(GO)SiO]_d$ wherein a+b+c+d is an integer of 6 to 24, a, b, c and d are each an integer of 0 or more, and a and/or b are/is an integer of 1 or more; X is a polysiloxanylalkyl group having an alkenyl group or a hydrosilyl group; W is a polysiloxanylalkylsilyl group having an alkenyl group or a hydrosilyl group; $R^1$ is an alkyl group or an aryl group; $R^2$ is an alkyl group, an aryl group, an alkenyl group, a hydrogen atom, or a group bonded to another polyhedral polysiloxane; and G is a hydrogen atom or a group represented by $SiR^2_3$.

20). The modified polyhedral polysiloxane according to 19), wherein the group X is represented by the formula (1) or (2):

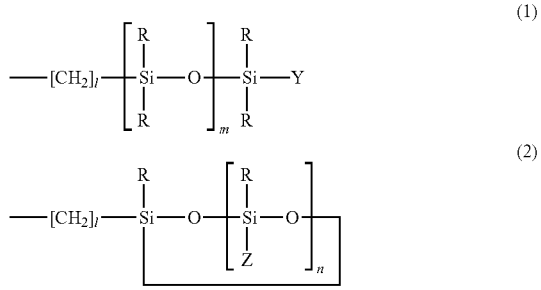

wherein l is an integer of 2 or more; m is an integer of 0 or more; n is an integer of 2 or more; Y is a hydrogen atom, an alkenyl group, an alkyl group, an aryl group, or a moiety bonded to a polyhedral polysiloxane via an alkylene chain, and the Ys may be the same as or different from each other; Z is a hydrogen atom, an alkenyl group, an alkyl group, an aryl group, or a moiety bonded to a polyhedral polysiloxane via an alkylene chain, and the Zs may be the same as or different from each other, provided that at least one of the Ys and Zs is a hydrogen atom or an alkenyl group; and R is an alkyl group or an aryl group, wherein in the case where there are a plurality of Xs, the structures of the formula (1) or (2) may be different from each other, or the structures of the formulas (1) and (2) may coexist.

21). The modified polyhedral polysiloxane according to 19) or 20), wherein the group W is represented by $SiR^1{}_2X$.

22). The modified polyhedral polysiloxane according to any one of 19) to 21), which is obtainable by: adding an excessive amount of the hydrosilyl group-containing compound (b) to the polyhedral polysiloxane compound (a) to allow the compound (a) to be modified with the compound (b) by a hydrosilylation reaction, wherein the number of a hydrogen atom directly bonded to a Si atom is 2.5 to 20 per one alkenyl group; and distilling off an unreacted portion of the hydrosilyl group-containing compound (b), the polyhedral polysiloxane compound (a) containing a siloxane unit represented by the formula:

wherein a+b+c+d is an integer of 6 to 24, a, b, c and d are each an integer of 0 or more, and a and/or b are/is an integer of 1 or more; A is an alkenyl group or a hydrogen atom; D is a group represented by $SiR^1{}_2A$; at least one of the As is an alkenyl group; $R^1$ is an alkyl group or an aryl group; and G is a hydrogen atom or a group represented by $-SiR^1{}_3$.

23). The modified polyhedral polysiloxane according to any one of 19) to 21), which is obtainable by: adding an excessive amount of the alkenyl group-containing compound (b) to the polyhedral polysiloxane compound (a) to allow the compound (a) to be modified with the compound (b) by a hydrosilylation reaction, wherein the number of an alkenyl group is 2.5 to 20 per one hydrogen atom directly bonded to a Si atom; and distilling off an unreacted portion of the hydrosilyl group-containing compound (b), the polyhedral polysiloxane compound (a) containing a siloxane unit represented by the formula:

wherein a+b+c+d is an integer of 6 to 24, a, b, c and d are each an integer of 0 or more, and a and/or b are/is an integer of 1 or more; U is an alkenyl group or a hydrogen atom; E is a group represented by $SiR^1{}_2U$; at least one of the Us is a hydrosilyl group; $R^1$ is an alkyl group or an aryl group; and G is a hydrogen atom or a group represented by $-SiR^1{}_3$.

24). A modified polyhedral polysiloxane containing an epoxy group, which is obtainable by: modifying, with an epoxy compound (c) having a carbon-carbon unsaturated bond, the modified polyhedral polysiloxane according to any one of 1) to 23) that is obtainable by modifying the alkenyl group-containing polyhedral polysiloxane compound (a) with the hydrosilyl group-containing compound (b).

25). The modified polyhedral polysiloxane according to 24), wherein the epoxy group of the epoxy compound (c) having a carbon-carbon unsaturated bond is an alicyclic epoxy group and/or a glycidyl group.

26). The modified polyhedral polysiloxane according to 24) or 25), wherein the epoxy compound (c) having a carbon-carbon unsaturated bond contains one carbon-carbon unsaturated bond per molecule.

27). The modified polyhedral polysiloxane according to any one of 24) to 26), wherein a molecule of the modified polyhedral polysiloxane contains at least two hydrosilyl groups.

28). The modified polyhedral polysiloxane according to any one of 24) to 27), wherein the modified polyhedral polysiloxane is in a liquid state at 20° C.

29). A modified polyhedral polysiloxane, comprising a constitutional unit represented by the formula:

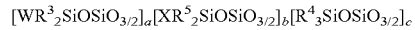

wherein a+b+c is an integer of 6 to 24, a is an integer of 1 or more, and b and c are each 0 or an integer of 1 or more; $R^3$ and $R^5$ are each an alkyl group or an aryl group; $R^4$ is a substituent group other than an alkenyl group and a hydrogen atom, such as an alkyl group, an aryl group, or a group bonded to another polyhedral polysiloxane or siloxane compound; W is a group having a structure represented by the following formula (3) or (4), wherein in the case where there are a plurality of Ws, the structures of the formula (3) or (4) may be different from each other, or the structures of the formulas (3) and (4) may coexist; and X is a group having a structure represented by the following formula (5) or (6), wherein in the case where there are a plurality of Xs, the structures of the formula (5) or (6) may be different from each other, or the structures of the formulas (5) and (6) may coexist,

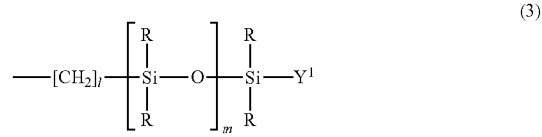

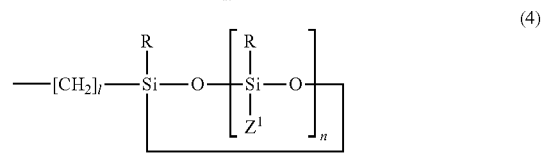

wherein l is an integer of 2 or more; m is an integer of 0 or more; n is an integer of 2 or more; R is an alkyl group or an aryl group; $Y^1$ is an epoxy group-containing group, a hydrogen atom, an alkenyl group, an alkyl group, or an aryl group, and the $Y^1$s may be the same as or different from each other; and $Z^1$ is an epoxy group-containing group, a hydrogen atom, an alkenyl group, an alkyl group, or an aryl group, and the $Z^1$s may be the same as or different from each other, provided that at least one of the $Y^1$s and $Z^1$s is an epoxy group-containing group,

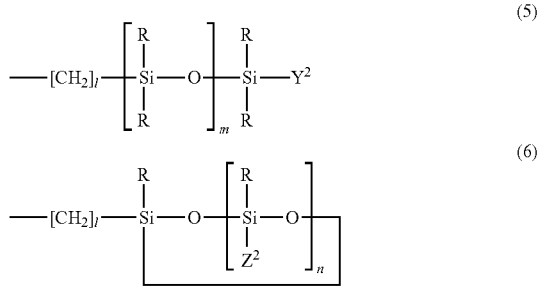

wherein l is an integer of 2 or more; m is an integer of 0 or more; n is an integer of 2 or more; R is an alkyl group or an aryl group; $Y^2$ is a hydrogen atom, an alkenyl group, an alkyl group, or an aryl group, and the $Y^2$s may be the same as or different from each other; and $Z^2$ is a hydrogen atom, an alkenyl group, an alkyl group, or an aryl group, and the $Z^2$s may be the same as or different from each other, provided that at least one of the $Y^2$s and $Z^2$s is a hydrogen atom.

30). A polysiloxane composition, comprising: the modified polyhedral polysiloxane according to any one of 1) to 29); and a curing initiator.

31). The polysiloxane composition according to 30), wherein the curing initiator is a photo-curing initiator.

31). The polysiloxane composition according to 31), wherein the photo-curing initiator is an onium salt.

33). A polysiloxane composition, comprising: the modified polyhedral polysiloxane according to any one of 1) to 29); and a curing agent.

34). The polysiloxane composition according to any one of 30) to 33), further comprising a hydrosilylation catalyst.

35). The polysiloxane composition according to any one of 30) to 34), further comprising a curing retardant.

36). The polysiloxane composition according to any one of 30) to 35), further comprising an adhesion promoter.

37). The polysiloxane composition according to 36), wherein the adhesion promoter is a silane coupling agent.

38). The polysiloxane composition according to 37), wherein the adhesion promoter is a silane coupling agent containing, in the molecule, a hydrolyzable silicate group and at least one functional group selected from the group consisting of an epoxy group, a methacryl group, an acryl group, an isocyanate group, an isocyanurate group, a vinyl group, and a carbamate group.

39). The polysiloxane composition according to any one of 30) to 38), further comprising an inorganic filler.

40). The polysiloxane composition according to any one of 33) to 39), wherein the modified polyhedral polysiloxane is the modified polyhedral polysiloxane according to any one of 1) to 29) obtained by modifying the alkenyl group-containing polyhedral polysiloxane compound (a) with the hydrosilyl group-containing compound (b), and the curing agent comprises an alkenyl group-containing polysiloxane with a molecular weight less than 3000 and an alkenyl group-containing polysiloxane with a molecular weight of 5000 or more.

41). A cured product, which is obtainable by curing the polysiloxane composition according to any one of 30) to 40).

42). An encapsulant for optical elements, comprising the modified polyhedral polysiloxane according to any one of 1) to 29).

43). An encapsulant for optical elements, which is prepared using the polysiloxane composition according to any one of 30) to 40).

44). A composition for optical elements, comprising the modified polyhedral polysiloxane according to any one of 1) to 29).

45). A composition for optical elements, which is prepared using the polysiloxane composition according to any one of 30) to 40).

46). An insulator, comprising the modified polyhedral polysiloxane according to any one of 1) to 29).

47). An insulator, which is prepared using the polysiloxane composition according to any one of 30) to 40).

The present invention can provide a modified product, particularly in liquid form, of polyhedral polysiloxane, which is excellent in moldability, transparency, heat resistance, light resistance, and adhesiveness, and a composition produced using the modified product. The present invention can also provide a modified polyhedral polysiloxane having alkali solubility and having excellent heat and light resistances.

BEST MODE FOR CARRYING OUT THE INVENTION

The present invention will be specifically described bellow.
<Modified Polyhedral Polysiloxane>

The modified polyhedral polysiloxane of the present invention can be provided by modifying a polyhedral polysiloxane compound (a) having an alkenyl group and/or a hydrosilyl group with a compound (b) having a hydrosilyl group and/or an alkenyl group that are/is capable of hydrosilylation with the component (a). A feature of the present invention is that no gelation occurs upon synthesis of a modified product. Advantageously, a modified polyhedral polysiloxane to be provided may be in a liquid state at 20° C. from handleability and moldability viewpoints.

From easy production and productivity viewpoints, the modified polyhedral polysiloxane of the present invention is desirably a modified product provided by modifying an alkenyl group-containing polyhedral polysiloxane compound (a) with a hydrosilyl group-containing compound (b).

The desirable modified polyhedral polysiloxane of the present invention will be specifically described below. The desirable modified polyhedral polysiloxane of the present invention contains a reactive functional group-containing siloxane unit $[XR^1{}_2SiO—SiO_{3/2}]$ as an essential unit. If necessary, the desirable modified polyhedral polysiloxane may contain, as a constitutional unit, a silanol group-containing siloxane unit $[HO—SiO_{3/2}]$ or an optional siloxane unit $[R^2{}_3SiO—SiO_{3/2}]$ that serves as a unit for controlling physical properties. For example, the desirable modified polyhedral polysiloxane contains a siloxane unit represented by the formula:

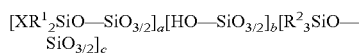

wherein
a+b+c is an integer of 6 to 24, a is an integer of 1 or more, and b and c are each 0 or an integer of 1 or more;
X is a reactive functional group-containing group;
$R^1$ is an alkyl group or an aryl group; and
$R^2$ is an alkyl group, an aryl group, an alkenyl group, a hydrogen atom, or a group bonded to another polyhedral polysiloxane. Here, a is 1 or more, and desirably 2 or more, on average; b and c are each 0 or an integer of 1 or more; and a+b+c is an integer of 6 to 24, and desirably an integer of 6 to 12.

The reactive functional group-containing siloxane unit $[XR^1{}_2SiO—SiO_{3/2}]$ will be described below.

The reactive functional group-containing siloxane unit effects a cross-linking reaction with a curing agent by hydrosilylation in the presence of the below-mentioned hydrosilylation catalyst, or effects cross-linking and curing in the presence of a thermosetting initiator or a photo-curing initiator.

The desirable reactive functional group-containing group X is not particularly limited as long as it is represented by either the formula (1) or (2), wherein m is desirably an integer of 1 to 7, and n is desirably an integer of 2 to 4.

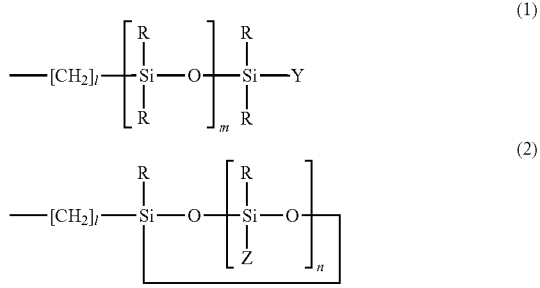

wherein
l is an integer of 2 or more;
m is an integer of 0 or more;
n is an integer of 2 or more;
Y is a hydrogen atom, an alkenyl group, an alkyl group, an aryl group, or a moiety bonded to a polyhedral polysiloxane via an alkylene chain, and the Ys may be the same as or different from each other;
Z is a hydrogen atom, an alkenyl group, an alkyl group, an aryl group, or a moiety bonded to a polyhedral polysiloxane via an alkylene chain, and the Zs may be the same as or different from each other, provided that at least one of the Ys and Zs is an alkenyl group or a hydrogen atom; and
R is an alkyl group or an aryl group, and
wherein in the case where there are a plurality of Xs, the structures of the formula (1) or (2) may be different from each other, or the structures of the formulas (1) and (2) may coexist.

Other examples of the reactive functional group in the desirable reactive functional group-containing group X include an epoxy group, a hydrolyzable silyl group, an oxetanyl group, a (meth)acryloyl group, and a thiol group. Desirable examples of X include groups containing the above-mentioned reactive functional groups.

In the case where the reactive functional group is an epoxy group, a hydrolyzable silyl group, or an oxetanyl group, the reactive functional group-containing group X may be allowed to be cross-linked in the presence of an acid generator or a cationic polymerization initiator. In the case where the reactive functional group is a (meth)acryloyl group or a thiol group, the reactive functional group-containing group X may be allowed to be cross-linked in the presence of a radical generator. In particular, an epoxy group, a hydrolyzable silyl group, and an oxetanyl group as reactive functional groups are less susceptible to oxygen inhibition. The groups X containing these groups are suitably used because such groups X tend to exert sufficient adhesiveness to a substrate, for example. In particular, a hydrolyzable silyl group-containing group X is suitably used from the viewpoints of heat and light resistances.

Specific examples of the hydrolyzable silyl group include, but are not limited to, halogenated silyl groups such as a trichlorosilyl group, a methyldichlorosilyl group, a dimethylchlorosilyl group, and a phenyldichlorosilyl group; alkoxysilyl groups such as a trimethoxysilyl group, a triethoxysilyl group, a methyldiethoxysilyl group, a methyldimethoxysilyl group, and a phenyldimethoxysilyl group; acyloxysilyl groups such as a methyldiacetoxysilyl group and a phenyldiacetoxysilyl group; and ketoximatesilyl groups such as a bis(dimethylketoximate)methylsilyl group and a bis(cyclohexylketoximate)methylsilyl group. Particularly suitable among these are alkoxysilyl groups from the viewpoints of reactivity, handleability, and properties of cured products to be provided.

In the reactive functional group-containing siloxane unit, $R^1$ may be a substantially-nonreactive substituent such as an alkyl group or an aryl group.

On average, two or more siloxane units among all of the siloxane units in the polyhedral framework are desirably the reactive functional group-containing siloxane units of the present invention. In other words, a in the formula (1) is desirably 2 or more. Curability may be insufficient and the strength of a cured product to be obtained may be low in the case where the modified polyhedral polysiloxane contains a smaller number of the reactive functional group-containing siloxane units.

Next, the silanol group-containing siloxane unit [HO—$SiO_{3/2}$] will be described below.

In the silanol group-containing siloxane unit of the present invention, a hydroxy group (OH group) is directly bonded to a Si atom which forms a polyhedral framework. The silanol group-containing siloxane unit imparts solubility in an alkali developing solution to the modified polyhedral polysiloxane in order to impart alkali developability. The silanol group-containing unit is favorable also because the silanol group thereof is directly bonded to the polyhedral framework and thus it is not bonded via an organic ingredient which reduce heat and light resistances of the compound.

On average, one or more siloxane units among all of the siloxane units in the polyhedral framework are desirably the silanol group-containing siloxane units of the present invention. Alkali developability may be insufficient in the case where the modified polyhedral polysiloxane contains a smaller number of the silanol group-containing siloxane units.

Next, the optional siloxane unit [$R^2_3$SiO—$SiO_{3/2}$] will be described below.

The optional siloxane unit controls physical properties of the modified polyhedral polysiloxane of the present invention and a cured product to be provided. The optional siloxane unit contains substantially no reactive substituent group, so that the unit makes it possible to control cross-linking density, and to improve coatability, leveling properties, and fragility.

Suitably used as $R^2$ in the optional siloxane unit is an alkyl group, an aryl group, an alkenyl group, a hydrogen atom, or a group bonded to another polyhedral polysiloxane. Examples of the alkyl group include a methyl group, an ethyl group, a propyl group, a butyl group, a cyclopentyl group, a cyclohexyl group, and a cycloheptyl group. The alkyl group may be partially substituted by a substantially-nonreactive substituent. A specific example of the alkyl group partially-substituted by a substantially-nonreactive substituent is a polysiloxanylalkyl group. Such a group makes it possible to impart leveling properties, coatability and compatibility with the below-mentioned curing agent or curing initiator. The group also makes it possible to provide the compound in liquid form.

Examples of the group bonded to another polyhedral polysiloxane include groups bonded thereto via a polymer ingredient such as polysiloxane, poly(meth)acrylate, or polyisobutylene.

With respect to the desirable modified polyhedral polysiloxane of the present invention, the following embodiment may be also possible and desirable. It will be specifically described below.

The desirable modified polyhedral polysiloxane of the present invention contains, as an essential unit, a reactive functional group-containing siloxane unit that is [XSiO$_{3/2}$] and/or [R$^1$(WO)SiO]. The desirable modified polyhedral polysiloxane may contain, as a constitutional unit, an optional siloxane unit [R$^2$SiO$_{3/2}$] or [R$^2$(GO)SiO] which is a unit for controlling physical properties. An example of the desirable modified polyhedral polysiloxane is a modified polyhedral polysiloxane containing siloxane units represented by the formula:

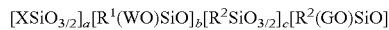

[XSiO$_{3/2}$]$_a$[R$^1$(WO)SiO]$_b$[R$^2$SiO$_{3/2}$]$_c$[R$^2$(GO)SiO]$_d$ wherein a+b+c+d is an integer of 6 to 24, a, b, c and d are each an integer of 0 or more, and a and/or b are/is an integer of 1 or more;

X is a polysiloxanylalkyl group having an alkenyl group or a hydrosilyl group;

W is a polysiloxanylalkylsilyl group having an alkenyl group or a hydrosilyl group;

R$^1$ is an alkyl group or an aryl group;

R$^2$ is an alkyl group, an aryl group, an alkenyl group, a hydrogen atom, or a group bonded to another polyhedral polysiloxane; and G is a hydrogen atom or a group represented by SiR$^2$$_3$.

Here, a, b, c and d are each an integer of 0 or more; a and/or b are/is 1 or more on average, and desirably 2 or more; and a+b+c+d is an integer of 6 to 24, and desirably an integer of 6 to 12.

The siloxane unit [XSiO$_{3/2}$] will be described below.

This siloxane unit effects a cross-linking reaction with a curing agent by hydrosilylation in the presence of the below-mentioned hydrosilylation catalyst, or effects cross-linking and curing in the presence of a thermosetting initiator or a photo-curing initiator. The functional group X is not particularly limited as long as it is represented by either the formula (1) or (2), wherein m is desirably an integer of 1 to 7, and n is desirably an integer of 2 to 4.

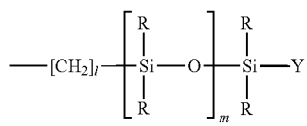

(1)

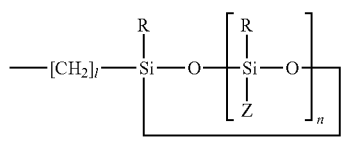

(2)

wherein l is an integer of 2 or more;

m is an integer of 0 or more;

n is an integer of 2 or more;

Y is a hydrogen atom, an alkenyl group, an alkyl group, an aryl group, or a moiety bonded to a polyhedral polysiloxane via an alkylene chain, and the Ys may be the same as or different from each other;

Z is a hydrogen atom, an alkenyl group, an alkyl group, an aryl group, or a moiety bonded to a polyhedral polysiloxane via an alkylene chain, and the Zs may be the same as or different from each other, provided that at least one of the Ys and Zs is a hydrogen atom or an alkenyl group; and R is an alkyl group or an aryl group; and wherein in the case where there are a plurality of Xs, the structures of the formula (1) or (2) may be different from each other, or the structures of the formulas (1) and (2) may coexist.

Next, the siloxane unit [R$^1$(WO)SiO] will be described below.

Similar to the aforementioned siloxane unit [XSiO$_{3/2}$], the siloxane unit [R$^1$(WO)SiO] effects a cross-linking reaction with a curing agent by hydrosilylation in the presence of the below-mentioned hydrosilylation catalyst. This siloxane unit effects a cross-linking reaction with a curing agent by hydrosilylation in the presence of the below-mentioned hydrosilylation catalyst, or effects cross-linking and curing in the presence of a thermosetting initiator or a photo-curing initiator. The reactive functional group W in the siloxane unit is a polysiloxanylalkylsilyl group having an alkenyl group or a hydrosilyl group. A specific example of the group suitably used is a group SiR$^1$$_2$X.

Suitably used as R$^1$ according to the present invention is an alkyl group or an aryl group. Examples of the alkyl group include a methyl group, an ethyl group, a propyl group, a butyl group, a cyclopentyl group, a cyclohexyl group, and a cycloheptyl group. The alkyl group may be partially substituted by a substantially-nonreactive substituent. A specific example of the alkyl group partially-substituted by a substantially-nonreactive substituent is a polysiloxanylalkyl group. Such a group makes it possible to impart leveling properties, coatability and compatibility with the below-mentioned curing agent. The group also makes it possible to provide the compound in liquid form.

Next, the optional siloxane unit [R$^2$SiO$_{3/2}$] will be described below.

This siloxane unit controls physical properties of the modified polyhedral polysiloxane of the present invention and a cured product to be provided. The siloxane unit contains substantially no reactive substituent group, so that the unit makes it possible to control cross-linking density, and to improve coatability, leveling properties, and fragility.

Suitably used as R$^2$ according to the present invention is an alkyl group, an aryl group, an alkenyl group, a hydrogen atom, or a group bonded to another polyhedral polysiloxane.

Examples of the alkyl group include a methyl group, an ethyl group, a propyl group, a butyl group, a cyclopentyl group, a cyclohexyl group, and a cycloheptyl group, and each of these groups may be partially substituted by a substantially-nonreactive substituent. A specific example of the alkyl group partially-substituted by a substantially-nonreactive substituent is a polysiloxanylalkyl group. Such a group makes it possible to impart leveling properties, coatability and compatibility with the below-mentioned curing agent. The group also makes it possible to provide the modified polyhedral polysiloxane in liquid form.

Examples of the group bonded to another polyhedral polysiloxane include groups bonded thereto via a polymer ingredient such as polysiloxane, poly(meth)acrylate, or polyisobutylene.

Next, the optional siloxane unit [R²(GO)SiO] will be described below.

The substituent group G in this siloxane unit of the present invention is a hydrogen atom and/or a group SiR²₃. In the case where G is a hydrogen atom, it is possible to impart solubility in an alkali developing solution to the modified polyhedral polysiloxane in order to impart alkali developability. If G is a group SiR²₃, it is possible to control physical properties such as cross-linking density of the below-mentioned cured product to be provided.

For achieving good adhesiveness to a substrate, the modified polyhedral polysiloxane is desirably an epoxy group-containing modified polyhedral polysiloxane which is obtainable by modifying, with an epoxy compound (c) having a carbon-carbon unsaturated bond, the modified polyhedral polysiloxane that is obtainable by modifying an alkenyl group-containing polyhedral polysiloxane compound (a) with a hydrosilyl group-containing compound (b).

<Production Method of Modified Polyhedral Polysiloxane>

The following will describe the method for producing the modified polyhedral polysiloxane according to the present invention.

First, the polyhedral polysiloxane compound (a) will be described below.

For example, the polyhedral polysiloxane compound (a) having an alkenyl group and/or a hydrosilyl group may be synthesized by the hydrolysis condensation reaction of a silane compound represented by the formula:

$R^3SiX^a_3$ wherein R³ is an alkenyl group or a hydrogen atom and $X^a$ is a hydrolyzable group such as a halogen atom or an alkoxy group. Alternatively, the compound (a) may be synthesized as follows: first, a trisilanol compound having three silanol groups in the molecule is synthesized by the hydrolysis condensation reaction of $R^3SiX^a_3$; and then, the trisilanol compound is allowed to react with a trifunctional silane compound that is the same as or different from the silane compound so as to close into a ring. Furthermore, a partially-cleaved polyhedral polysiloxane may be synthesized by reacting a monofunctional silane and/or a bifunctional silane with the trisilanol compound.

The polyhedral polysiloxane compound (a) may be synthesized by another method as exemplified below. First, a tetraalkoxysilane such as tetraethoxysilane is subjected to a hydrolysis condensation reaction in the presence of a base such as a quaternary ammonium hydroxide (e.g. trimethyl(2-hydroxyethyl)ammonium hydroxide or tetramethylammonium hydroxide) to provide a polyhedral silicate, and then the provided silicate is allowed to react with a silylating agent such as a silyl chloride having an alkenyl group and/or a hydrosilyl group to provide the polyhedral polysiloxane compound (a). In the present invention, silica or silica-containing materials such as rice hulls instead of tetraalkoxysilane may be used for obtaining the similar polyhedral siloxane.

A specific example of the desirable polyhedral polysiloxane compound (a) of the present invention is an alkenyl group-containing polyhedral polysiloxane compound represented by the formula:

[AR¹₂SiO—SiO₃/₂]ₐ[R⁴₃SiO—SiO₃/₂]ᵦ wherein
a+b is an integer of 6 to 24, a is an integer of 1 or more, and b is 0 or an integer of 1 or more;
As are alkenyl group(s) and/or hydrogen atom(s), provided that at least one of the As is an alkenyl group;
R¹ is an alkyl group or an aryl group; and
R⁴ is a substituent group other than an alkenyl group and a hydrogen atom, such as an alkyl group, an aryl group, or a group bonded to another polyhedral polysiloxane or siloxane compound.

In the case of using the aforementioned component (a), use of a hydrosilyl group-containing compound as the component (b) makes it possible to provide a modified polyhedral polysiloxane by, for example, hydrosilylation in the presence of the below-mentioned hydrosilylation catalyst. At this time, not all of the alkenyl groups in the polyhedral polysiloxane compound (a) are required to react, and a part of the alkenyl groups may remain. A plurality of the polyhedral polysiloxane compounds (a) may react with a plurality of the hydrosilyl group-containing compounds (b).

Another specific example of the desirable polyhedral polysiloxane compound (a) of the present invention is a polyhedral polysiloxane compound represented by the formula:

[BR¹₂SiO—SiO₃/₂]ₐ[R⁴₃SiO—SiO₃/₂]ᵦ wherein
a+b is an integer of 6 to 24, a is an integer of 1 or more, and b is 0 or an integer of 1 or more;
Bs are alkenyl group(s) and/or hydrogen atom(s), provided that at least one of the Bs is a hydrogen atom;
R¹ is an alkyl group or an aryl group; and
R⁴ is a substituent group other than an alkenyl group and a hydrogen atom, such as an alkyl group, an aryl group, or a group bonded to another polyhedral polysiloxane or siloxane compound.

In the case of using the aforementioned component (a), use of an alkenyl group-containing compound as the component (b) makes it possible to provide a modified polyhedral polysiloxane by, for example, hydrosilylation in the presence of the below-mentioned hydrosilylation catalyst. At this time, not all of the hydrogen atoms in the polyhedral polysiloxane compound (a) are required to react, and a part of the hydrogen atoms may remain. A plurality of the polyhedral polysiloxane compounds (a) may react with a plurality of the alkenyl group-containing compounds (b).

Another specific example of the desirable polyhedral polysiloxane compound (a) of the present invention is an alkenyl group-containing polyhedral polysiloxane compound represented by the formula:

[ASiO₃/₂]ₐ[R¹(DO)SiO]ᵦ[R¹SiO₃/₂]_c[R¹(GO)SiO]_d wherein
a+b+c+d is an integer of 6 to 24, a, b, c and d are each an integer of 0 or more, and a and/or b are/is an integer of 1 or more;
A is an alkenyl group or a hydrogen atom;
D is a group SiR¹₂A;
at least one of the As is an alkenyl group;
R¹ is an alkyl group or an aryl group; and
G is a hydrogen atom or a group —SiR¹₃.

In the case of using the aforementioned component (a), use of a hydrosilyl group-containing compound as the component (b) makes it possible to provide a modified polyhedral polysiloxane by, for example, hydrosilylation in the presence of the below-mentioned hydrosilylation catalyst. At this time, not all of the alkenyl groups in the polyhedral polysiloxane compound (a) are required to react, and a part of the alkenyl groups may remain. A plurality of the polyhedral polysiloxane compounds (a) may react with a plurality of the hydrosilyl group-containing compounds (b).

Another specific example of the desirable polyhedral polysiloxane compound (a) of the present invention is a polyhedral polysiloxane compound represented by the formula:

[USiO₃/₂]ₐ[R¹(EO)SiO]ᵦ[R¹SiO₃/₂]_c[R¹(GO)SiO]_d wherein
a+b+c+d is an integer of 6 to 24, a, b, c and d are each an integer of 0 or more, and a and/or b are/is an integer of 1 or more;
U is an alkenyl group or a hydrogen atom;
E is a group $SiR^1_2U$;
at least one of the Us is a hydrogen group;
$R^1$ is an alkyl group or an aryl group; and
G is a hydrogen atom or a group $SiR^1_3$.

In the case of using the aforementioned component (a), use of an alkenyl group-containing compound as the component (b) makes it possible to provide a modified polyhedral polysiloxane by, for example, hydrosilylation in the presence of the below-mentioned hydrosilylation catalyst. At this time, not all of the hydrogen atoms in the polyhedral polysiloxane compound (a) are required to react, and a part of the hydrogen atoms may remain. A plurality of the polyhedral polysiloxane compounds (a) may react with a plurality of the alkenyl group-containing compounds (b).

Next, the compound (b) having a hydrosilyl group and/or an alkenyl group will be described below.

The hydrosilyl group-containing compound is a compound that has a hydrosilyl group (a hydrogen atom directly bonded to a Si atom) and reacts with the alkenyl group of the polyhedral polysiloxane compound (a) to newly introduce a reactive functional group-containing group into the polyhedral polysiloxane molecule.

A specific example of the desirable hydrosilyl group-containing compound of the present invention is a compound that has a hydrosilyl group (a hydrogen atom directly bonded to a Si atom) and reacts with the alkenyl group of the polyhedral polysiloxane compound (a) to form a reactive functional group X represented by either the formula (1) or (2)

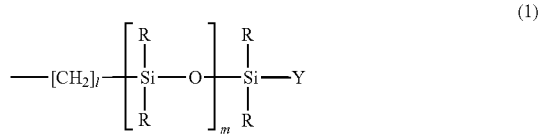

(1)

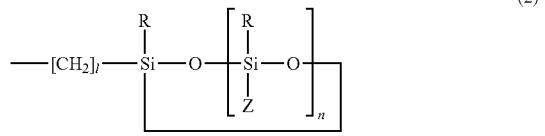

(2)

wherein
l is an integer of 2 or more;
m is an integer of 0 or more;
n is an integer of 2 or more;
Y is a hydrogen atom, an alkenyl group, an alkyl group, an aryl group, or a moiety bonded to a polyhedral polysiloxane via an alkylene chain, and the Ys may be the same as or different from each other;
Z is a hydrogen atom, an alkenyl group, an alkyl group, an aryl group, or a moiety bonded to a polyhedral polysiloxane via an alkylene chain, and the Zs may be the same as or different from each other, provided that at least one of the Ys and Zs is a hydrogen atom; and
R is an alkyl group or an aryl group, and
wherein in the case where there are a plurality of Xs, the structures of the formula (1) or (2) may be different from each other, or the structures of the formulas (1) and (2) may coexist.

Examples of the hydrosilyl group-containing compound include hydrosilyl group-containing siloxane compounds, and desirable examples thereof include, specifically, linear polysiloxanes having hydrosilyl groups at the both ends and hydrosilyl group-containing cyclic siloxanes. The hydrosilyl group-containing cyclic siloxanes are more desirable. Each of these hydrosilyl group-containing compounds may be used singly or two or more of these may be used in combination.

Specific examples of the linear polysiloxanes having hydrosilyl groups at the both ends include a poly- or oligosiloxane with the ends terminated by dimethylhydrogensilyl groups, tetramethyldisiloxane, and hexamethyltrisiloxane.

Examples of the hydrosilyl group-containing cyclic siloxanes include 1,3,5,7-tetrahydrogen-1,3,5,7-tetramethylcyclotetrasiloxane, 1-propyl-3,5,7-trihydrogen-1,3,5,7-tetramethylcyclotetrasiloxane, 1,5-dihydrogen-3,7-dihexyl-1,3,5,7-tetramethylcyclotetrasiloxane, 1,3,5-trihydrogen-trimethylcyclosiloxane, 1,3,5,7,9-pentahydrogen-1,3,5,7,9-pentamethylcyclosiloxane, and 1,3,5,7,9,11-hexahydrogen-1,3,5,7,9,11-hexamethylcyclosiloxane.

The hydrosilyl group-containing compound (b), in particular, a hydrosilyl group-containing siloxane compound, is desirably used in such an amount that the number of a hydrogen atom directly bonded to a Si atom of the compound (b) is 2.5 to 20 per one alkenyl group of the polyhedral polysiloxane compound (a); however, the amount thereof depends on the kind of the compound used. A smaller amount of the compound (b) may cause gelation by a cross-linking reaction, thereby providing a modified polysiloxane with poor handleability. A larger amount of the compound (b) may have a bad influence on physical properties of a cured product. Since an excessive amount of the hydrosilyl group-containing siloxane compound is used, it is desirable to remove an unreacted portion of the hydrosilyl group-containing siloxane compound, for example, under vacuum and heated conditions.

Other examples of the desirable hydrosilyl group-containing compound (b) include hydrosilyl group-containing compounds having at least one reactive functional group selected from the group consisting of an epoxy group, a hydrolyzable silyl group, an oxetanyl group, a (meth)acryloyl group, and a thiol group.

The hydrosilyl group-containing compound having a reactive functional group is desirably used in such an amount that the number of a hydrogen atom directly bonded to a Si atom of the hydrosilyl group-containing compound is 0.2 to 1.5 per one alkenyl group of the polyhedral siloxane intermediate; however, the amount thereof depends on the kind of the compound used. A smaller amount thereof may cause a low introduction rate of reactive functional groups and this may have a bad influence on physical properties of a cured product to be provided. A larger amount of the hydrosilyl group-containing compound having a reactive functional group may result in unreacted residues thereof and this may have a bad influence on physical properties of a cured product.

The alkenyl group-containing compound (b) mentioned above is a compound that has an alkenyl group and reacts with the hydrosilyl group of the polyhedral polysiloxane compound (a) to introduce a new functional group into the polyhedral polysiloxane molecule.

Examples of the alkenyl group-containing compound (b) include alkenyl group-containing siloxane compounds, and desirable examples thereof include, specifically, linear polysiloxanes having alkenyl groups at the both ends and alkenyl group-containing cyclic siloxanes. Each of these hydrosilyl group-containing compounds may be used singly or two or more of these may be used in combination.

Specific examples of the linear polysiloxanes having alkenyl groups at the both ends include a poly- or oligo-siloxane with the ends terminated by dimethylvinylsilyl groups, tetramethyldivinyldisiloxane, and hexamethyldivinyltrisiloxane.

Examples of the alkenyl group-containing cyclic siloxanes include 1,3,5,7-tetravinyl-1,3,5,7-tetramethylcyclotetrasiloxane, 1-propyl-3,5,7-trivinyl-1,3,5,7-tetramethylcyclotetrasiloxane, 1,5-divinyl-3,7-dihexyl-1,3,5,7-tetramethylcyclotetrasiloxane, 1,3,5-trivinyl-trimethylcyclosiloxane, 1,3,5,7,9-pentavinyl-1,3,5,7,9-pentamethylcyclosiloxane, and 1,3,5,7,9,11-hexavinyl-1,3,5,7,9,11-hexamethylcyclosiloxane.

The alkenyl group-containing compound (b), in particular, an alkenyl group-containing siloxane compound, is desirably used in such an amount that the number of an alkenyl group of the compound (b) is 2.5 to 20 per one hydrogen atom directly bonded to a Si atom of the polyhedral siloxane intermediate; however, the amount thereof depends on the kind of the compound used. A smaller amount of the compound (b) may cause gelation by a cross-linking reaction, thereby providing a modified polysiloxane with poor handleability. A larger amount of the compound (b) may have a bad influence on physical properties of a cured product.

Other examples of the desirable alkenyl group-containing compound include alkenyl group-containing compounds having at least one reactive functional group selected from the group consisting of an epoxy group, a hydrolyzable silyl group, an oxetanyl group, a (meth)acryloyl group, and a thiol group.

The alkenyl group-containing compound having a reactive functional group is desirably used in such an amount that the number of a hydrogen atom directly bonded to a Si atom of the alkenyl group-containing compound is 0.2 to 1.5 per one alkenyl group of the polyhedral siloxane intermediate; however, the amount thereof depends on the kind of the compound used. A smaller amount thereof may cause a low introduction rate of reactive functional groups and this may have a bad influence on physical properties of a cured product to be provided. A larger amount of the alkenyl group-containing compound having a reactive functional group may result in unreacted residues thereof and this may have a bad influence on physical properties of a cured product.

In the present invention, groups on the Si atoms desirably comprise a hydrogen atom, a vinyl group, and a methyl group from the viewpoints of heat and light resistances.

The modified polyhedral polysiloxane of the present invention is desirably in a liquid state from the viewpoints such as handleability upon preparing a cured product, and is desirably transparent from the viewpoint of the light transmittance of a molded product.

Next, the following will describe the method for producing a modified polyhedral polysiloxane having a silanol group-containing siloxane unit [HO—SiO$_{3/2}$].

(I) Synthesis Method of Polyhedral Siloxane Intermediate

In the present invention, a desirable example of an intermediate for efficiently providing a desired modified polyhedral polysiloxane is represented by the formula:

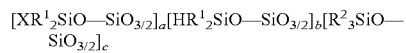

wherein
a+b+c is an integer of 6 to 24, a and b are each an integer of 1 or more, and c is 0 or an integer of 1 or more;
X is any reactive functional group-containing group;
R$^1$ is an alkyl group or an aryl group;
R$^2$ is an alkyl group, an aryl group, or a group bonded to another polyhedral polysiloxane.

Surprisingly, the group HR$^1{}_2$SiO of the siloxane unit [HR$^1{}_2$SiO—SiO$_{3/2}$] in the intermediate can be highly selectively and effectively converted to a silanol group by treatment with the below-mentioned polar solvent or water to provide a target compound in good yield.

The polyhedral siloxane intermediate may be synthesized by any method.

Specifically, for example, a tetraalkoxysilane such as tetraethoxysilane is subjected to a hydrolysis condensation reaction in the presence of a base such as quaternary ammonium hydroxide to provide a polyhedral silicate. Then, the provided silicate is allowed to react with a silylating agent such as dimethylsilyl chloride to provide a polyhedral siloxane compound (a) as a precursor of the intermediate.

The silylating agent is required to be used at least in consideration of introductions of a silanol group and of the reactive functional group-containing group X. With respect to the introduction of a silanol group, it is desirable to introduce a group HR$^1{}_2$SiO in an amount at least equivalent to the target introduction amount of a silanol group.

The introduction of the reactive functional group-containing group may be performed by any method, and may be desirably performed by modifying the precursor of the polyhedral siloxane intermediate by any reaction.

Specifically, the introduction of the reactive functional group-containing group is performed, for example, by synthesizing the precursor of a polyhedral siloxane intermediate represented by the formula:

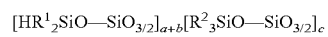

in which an excessive amount of a group HR$^1{}_2$SiO is introduced relative to a desired introduction amount of a silanol group;

and modifying an excess amount (corresponding to "a" in the formula) of the group HR$^1{}_2$SiO in the precursor with an ingredient (compound) for introducing the reactive functional group-containing group X by a reaction such as a hydrosilylation reaction to introduce the reactive functional group.

(II) Introduction of Silanol Group by Removal of Dimethylsiloxy Group

To the polyhedral siloxane intermediate obtained in (I), represented by the formula:

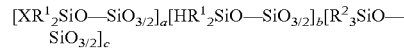

wherein
a+b+c is an integer of 6 to 24, a and b are each an integer of 1 or more, and c is 0 or an integer of 1 or more;
X is any reactive functional group;
R$^1$ is an alkyl group or a phenyl group; and
R$^2$ is an alkyl group, a phenyl group, or a group bonded to another polyhedral polysiloxane,
is added a polar solvent, desirably, methanol, ethanol, tetrahydrofuran, acetone, methylethylketone or like solvent, and then the mixture is stirred. Thereby, the target compound is generated. In the process, a small amount of water may be optionally added, and/or heating may be optionally performed. Distillation of the solvent after the reaction enables isolation in good yield of the polyhedral polysiloxane intermediate of the present invention represented by the following formula:

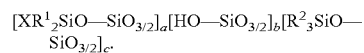

Furthermore, an epoxy group-containing modified polyhedral polysiloxane is desirable because of its high adhesiveness to a substrate. The epoxy group-containing modified polyhedral polysiloxane is obtainable by modifying, with an epoxy compound (c) having a carbon-carbon unsaturated bond, the modified polyhedral polysiloxane that is obtainable by modifying an alkenyl group-containing polyhedral polysiloxane compound (a) with a hydrosilyl group-containing compound (b).

The modification of the modified polyhedral polysiloxane with the epoxy compound (c) having a carbon-carbon unsaturated bond may be achieved by the hydrosilylation reaction used according to the present invention.

This modified polyhedral polysiloxane may be any one of the aforementioned modified polyhedral polysiloxanes, or may be the product provided by each of the production methods of the aforementioned modified polyhedral polysiloxanes.

<Epoxy Compound (c) Having Carbon-Carbon Unsaturated Bond>

The epoxy compound (c) having a carbon-carbon unsaturated bond of the present invention is not particularly limited as long as the compound has at least one carbon-carbon unsaturated bond and at least one epoxy group in the molecule. Suitably used is a compound having one carbon-carbon unsaturated bond in the molecule.

With respect to the epoxy group, an alicyclic epoxy group or a glycidyl group can be suitably used from the viewpoint of adhesiveness to a substrate. Specifically, allylglycidyl ether and vinylcyclohexene oxide are suitably used.

Each of the above compounds may be used singly or two or more of these may be used in combination.

A specific example of the desirable epoxy group-containing modified polyhedral polysiloxane of the present invention is, from the viewpoints of heat and light resistances, or the strength of a cured product to be provided, a modified polysiloxane having a constitutional unit represented by the formula:

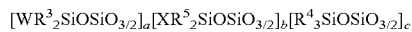

wherein
a+b+c is an integer of 6 to 24, a is an integer of 1 or more, and b and c are each 0 or an integer of 1 or more;
$R^3$ and $R^5$ are each an alkyl group or an aryl group;
$R^4$ is a substituent group other than an alkenyl group and a hydrogen atom, such as an alkyl group, an aryl group, or a group bonded to another polyhedral polysiloxane or siloxane compound;
W is a group having a structure represented by the following formula (3) or (4), wherein in the case where there are a plurality of Ws, the structures of the formula (3) or (4) may be different from each other, or the structures of the formulas (3) and (4) may coexist;
X is a group having a structure represented by the following formula (5) or (6), wherein in the case where there are a plurality of Xs, the structures of the formula (5) or (6) may be different from each other, or the structures of the formulas (5) and (6) may coexist,

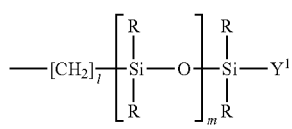

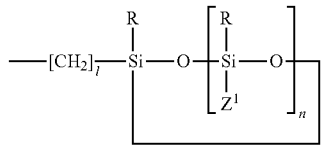

wherein
l is an integer of 2 or more;
m is an integer of 0 or more;
n is an integer of 2 or more;
R is an alkyl group or an aryl group;
$Y^1$ is an epoxy group-containing group, a hydrogen atom, an alkenyl group, an alkyl group, or an aryl group, and the $Y^1$s may be the same as or different from each other; and
$Z^1$ is an epoxy group-containing group, a hydrogen atom, an alkenyl group, an alkyl group, or an aryl group, and the $Z^1$s may be the same as or different from each other, provided that at least one of the $Y^1$s and $Z^1$s is an epoxy group-containing group,

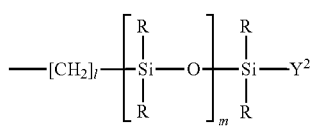

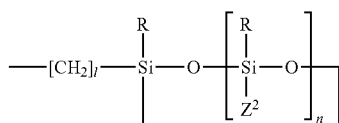

wherein
l is an integer of 2 or more;
m is an integer of 0.0 or more;
n is an integer of 2 or more;
R is an alkyl group or an aryl group;
$Y^2$ is a hydrogen atom, an alkenyl group, an alkyl group, or an aryl group, and the $Y^2$s may be the same as or different from each other; and
$Z^2$ is a hydrogen atom, an alkenyl group, an alkyl group, or an aryl group, and the $Z^2$s may be the same as or different from each other, provided that at least one of the $Y^2$s and $Z^2$s is a hydrogen atom.

Desirably, the epoxy group-containing modified polyhedral polysiloxane further has a hydrosilyl group in the molecule. The hydrosilyl group makes it possible to provide a cured product by the combined use with the below-mentioned curing agent, in particular an alkenyl group-containing compound, as well as to exert adhesiveness to a substrate. The epoxy group-containing modified polyhedral polysiloxane desirably has two or more hydrosilyl groups.

The modified polyhedral polysiloxane of the present invention is desirably in a liquid state from the viewpoints such as handleability upon preparing a cured product from the below-mentioned composition, and is desirably transparent from the viewpoint of the light transmittance of a cured product.

<Hydrosilylation Catalyst>

Next, the hydrosilylation catalyst to be used in the present invention will be described below.

In the present invention, the hydrosilylation catalyst may be used upon synthesis of the modified polyhedral polysiloxane and upon curing of the composition produced using the modified polyhedral polysiloxane.

The hydrosilylation catalyst to be used in the present invention is not particularly limited, and any one such as generally-used hydrosilylation catalysts may be used.

Specific examples thereof include: platinum-olefin complexes; chloroplatinic acid; simple platinum; carriers (such as alumina, silica, and carbon black) that carrying solid platinum; platinum-vinylsiloxane complexes such as $Pt_n(ViMe_2SiOSiMe_2Vi)_n$ and $Pt[(MeViSiO)_4]_m$; platinum-phosphine complexes such as $Pt(PPh_3)_4$ and $Pt(PBu_3)_4$; platinum-phosphite complexes such as $Pt[P(OPh)_3]_4$ and $Pt[P(OBu)_3]_4$, wherein Me represents a methyl group, Bu represents a butyl group, Vi represents a vinyl group, Ph represents a phenyl group, and n and m each represent an integer; $Pt(acac)_2$; platinum-hydrocarbon composites as disclosed in U.S. Pat. No. 3,159,601 and U.S. Pat. No. 3,159,662 by Ashby et. al.; and platinum alcoholate catalysts as disclosed in U.S. Pat. No. 3,220,972 by Lamoreaux et. al.

Examples of catalysts other than the platinum compounds include $RhCl(PPh_3)_3$, $RhCl_3$, $Rh/Al_2O_3$, $RuCl_3$, $IrCl_3$, $FeCl_3$, $AlCl_3$, $PdCl_2 \cdot 2H_2O$, $NiCl_2$, and $TiCl_4$. Each of these catalysts may be used singly, or two or more of these may be used in combination. Desirable among these are chloroplatinic acid, platinum-olefin complexes, platinum-vinylsiloxane complexes, and $Pt(acac)_2$ from the viewpoint of catalytic activity.

The amount of the hydrosilylation catalyst to be used upon synthesis of the modified polyhedral polysiloxane and upon curing is not particularly limited. For example, the hydrosilylation catalyst may be used in an amount of $10^{-1}$ to $10^{-10}$ mol per 1 mol of the alkenyl group of the polyhedral polysiloxane compound (a). Desirably, the catalyst may be used in an amount of $10^{-4}$ to $10^{-8}$ mol. Since the hydrosilylation catalyst may absorb lights with short wavelengths, depending on the kind of the catalyst, a larger amount of the catalyst may reduce the light resistance of a cured product to be provided, and may foam the cured product. A smaller amount of the catalyst may cause failure to progress in the reaction, and thus the target product may not be provided.

The reaction temperature of the hydrosilylation reaction of the modified polyhedral polysiloxane is desirably 30° C. to 400° C., more desirably 40° C. to 250° C., and further more desirably 45° C. to 140° C. A lower reaction temperature may cause insufficient progress of the reaction, and a higher reaction temperature may cause gelation, and thus the handleability may be poor.

<Composition>

Next, the polysiloxane composition provided according to the present invention will be described below.

In the present invention, the polysiloxane composition may be provided by adding a curing agent, a hydrosilylation catalyst, a curing retardant, an adhesion promoter, an inorganic filler, and the like to the modified polyhedral polysiloxane. The polysiloxane composition may be also provided by adding a curing initiator to the modified polyhedral polysiloxane. Furthermore, a cured product that is favorable in adhesiveness to a substrate can be provided from the composition produced by adding the below-mentioned curing agent, hydrosilylation catalyst, and adhesion promoter to the modified polyhedral polysiloxane of the present invention, among the modified polyhedral polysiloxanes according to the present invention.

The polysiloxane composition of the present invention may be a transparent liquid composition. In particular, a liquid composition can be provided without a solvent by using a liquid modified polyhedral polysiloxane, and the liquid composition can be poured into a mold and cured by heat to easily provide a molded product. The transparent composition may be used as an optical composition.

For example, a molded product formed by curing the transparent liquid composition may have a transmittance of 75% or more at a wavelength of 400 nm when it has a thickness of 3 mm. The modified polyhedral polysiloxane is desirably in a liquid state so as to easily provide the polysiloxane composition of the present invention in a liquid state.

In the case where heat is applied upon curing a composition containing the modified polyhedral polysiloxane by a hydlosylilation reaction, the curing temperature is desirably 30° C. to 400° C., and more desirably 50° C. to 250° C. A higher curing temperature tends to cause poor appearance on a cured product to be provided. A lower curing temperature may cause insufficient curing. Curing may be performed using combinations between two or more temperature conditions.

Specifically, the curing temperature is desirably stepwise increased, for example, to 70° C., then to 120° C., and finally to 150° C., because such stepwise increase makes it possible to provide a favorable cured product. The curing time period may be set depending on the curing temperature, the amounts of a hydrosilylation catalyst to be used and a hydrosilyl group, and the combination of other ingredients of the present composition. For example, a favorable cured product may be provided by a curing reaction for, desirably 1 minute to 12 hours, more desirably 10 minutes to 10 hours, and particularly desirably 10 minutes to 2 hours.

<Curing Initiator>

In the present invention, the curing initiator triggers a cross-linking reaction of reactive functional groups of the modified polysiloxane provided according to the present invention and allows the modified polysiloxane to be cured.

Suitably used in the present invention are initiators that trigger a cross-linking reaction by heat application (thermosetting initiators) and/or initiators that trigger a cross-linking reaction by light irradiation (photo-curing initiators). Desirably used among these are photo-curing initiators.

The thermosetting initiator used in the present invention is not particularly limited. Examples thereof include azo initiators, peroxides, persulphates, redox initiators, and thermal cationic initiators.

Examples of the azo initiator include, but are not limited to, 2,2'-azobis(4-methoxy-2,4-dimethylvaleronitrile) (VAZO 33), 2,2'-azobis(2-amidinopropane)dihydrochloride (VAZO 50), 2,2'-azobis(2,4-dimethylvaleronitrile) (VAZO 52), 2,2'-azobis(isobutylonitrile) (VAZO 64), 2,2'-azobis-2-methylbutylonitrile (VAZO 67), and 1,1-azobis(1-cyclohexanecarbonitrile) (VAZO 88) (all of these are available from DuPont Chemical), and 2,2'-azobis(2-cyclopropylpropionitrile) and 2,2'-azobis(methylisobutylate) (V-601) (available from Wako Pure Chemical Industries, Ltd.).

Examples of the peroxide initiator include, but are not limited to, benzoyl peroxide, acetyl peroxide, lauroyl peroxide, decanoyl peroxide, dicetyl peroxydicarbonate, di(4-t-butylcyclohexyl)peroxydicarbonate (Perkadox 16S) (available from Akzo Nobel), di(2-ethylhexyl)peroxydicarbonate, t-butyl peroxypivalate (Lupersol 11) (available from Elf Atochem), t-butylperoxy-2-ethylhexanoate (Trigonox 21-050) (available from Akzo Nobel), and dicumyl peroxide.

Examples of the persulphate initiator include, but are not limited to, potassium persulphate, sodium persulphate, and ammonium persulphate.

Examples of the redox (reduction-oxidation) initiator include, but are not limited to: combinations of the persulphate initiator and a reductant such as sodium hydrogen metasulfite or sodium hydrogen sulfite; initiators derived from organic peroxides and tertiary amines, such as an initiator derived from benzoyl peroxide and dimethyl aniline; and initiators derived from organic hydroperoxides and transition metals, such as an initiator derived from cumene hydroperoxide and cobalt naphtate.

Examples of other initiators include, but are not limited to, pinacols such as tetraphenyl 1,1,2,2-ethanediol. A desirable thermal radical initiator is selected from the group consisting of the azo initiators and the peroxide initiators. More desirable examples thereof include 2,2'-azobis(methylisobutylate), t-butyl peroxypivalate, and di(4-t-butylcyclohexyl)peroxydicarbonate, and mixtures thereof.

Examples of the thermal cationic polymerization initiator include cationic or protonic acid catalysts such as sulfonium salts, ammonium salts, pyridinium salts, phosphonium salts, iodonium salts, triflic acid salts, trifluoroboron ether complexes, and boron trifluoride. These initiators can be referred to as latent curing catalysts because they are highly stable until generating cationic species by heating.

It has been known that the polymerization activity varies depending on the kind of a substituent group and the kind of an anion of an onium salt, and particularly with respect to the anion, the polymerization activity increases in the order: $BF^-<AsF_6^-<PF_6^-<SbF_6^-<B(C_6F_5)_4^-$. In addition, it has been known that combinations of an aluminum complex and a silanol compound and combinations of an aluminum complex and a specific phenol compound such as bisphenol S may serve as cationic polymerization catalysts.

Furthermore, some onium salts, which may serve as the below-mentioned photo-cationic initiator, generate cationic species by heat. These onium salts may be used as the thermal cationic polymerization initiators. Examples thereof include San-Aid series SI-60L, SI-80L, and SI-100L (produced by Sanshin Chemical Industry Co., Ltd.) and RHODORSIL PI2074 (produced by RHODIA). Desirable among these cationic polymerization initiators are aromatic onium salts from the viewpoints of handleability and the excellent balance between latency and curability.

The photo-curing initiator to be used in the present invention is a compound that generates an active substance that allows reactive functional groups of the polysiloxane compound to be cross-linked when irradiated with active energy rays such as visible lights, ultraviolet rays, infrared rays, X-rays, α-rays, β-rays, or γ-rays. Examples of the photo-curing initiator include photo-radical initiators, photo-anionic initiators, near-infrared-ray polymerization initiators, photo-acid generators, and photo-cationic initiators.

Examples of the photo-radical initiator include acetophenone, propiophenone, benzophenone, xanthol, fluorene, benzaldehyde, anthraquinone, triphenylamine, carbazole, 3-methylacetophenone, 4-methylacetophenone, 3-pentylacetophenone, 2,2-diethoxyacetophenone, 4-methoxyacetophenone, 3-bromoacetophenone, 4-allylacetophenone, p-diacetylbenzene, 3-methoxybenzophenone, 4-methylbenzophenone, 4-chlorobenzophenone, 4,4'-dimethoxybenzophenone, 4-chloro-4'-benzylbenzophenone, 3-chloroxanthone, 3,9-dichloroxanthone, 3-chloro-8-nonylxanthone, benzoin, benzoin methyl ether, benzoin butyl ether, bis(4-dimethylaminophenyl)ketone, benzyl methoxy ketal, 2-chlorothioxanthone, 2,2-dimethoxy-1,2-diphenylethan-1-one 1-hydroxy-cyclohexyl-phenyl-ketone, 2-hydroxy-2-methyl-1-phenyl-propan-1-one, 2-methyl-1-[4-(methylthio)phenyl]-2-morpholinopropan-1-one, 2-benzyl-2-dimethylamino-1-(4-morpholinophenyl)-butanone-1, and dibenzoyl.

Desirable among these are α-hydroxyketone compounds (such as benzoin, benzoin methyl ether, benzoin butyl ether, and 1-hydroxy-cyclohexyl-phenyl-ketone) and phenylketone derivatives (such as acetophenone, propiophenone, benzophenone, 3-methylacetophenone, 4-methylacetophenone, 3-pentylacetophenone, 2,2-diethoxyacetophenone, 4-methoxyacetophenone, 3-bromoacetophenone, 4-allylacetophenone, 3-methoxybenzophenone, 4-methylbenzophenone, 4-chlorobenzophenone, 4,4'-dimethoxybenzophenone, 4-chloro-4'-benzylbenzophenone, and bis(4-dimethylaminophenyl)ketone).

If necessary, the photo-radical initiator may be used with polymerization inhibitors and the like, for example, hydroquinone, hydroquinone monomethyl ether, benzoquinone, or p-t-butyl catechol.

Examples of the photo-anionic initiator include 1,10-diaminodecane, 4,4'-trimethylenedipiperazine, carbamates and derivatives thereof, cobalt-amine complexes, aminoxyimino compounds, and ammonium borates.

The near-infrared-ray polymerization initiator may be a near-infrared-ray absorptive cationic dye or the like.

A desirable example of the near-infrared-ray absorptive cationic dye is a complex of a borate anion and a near-infrared-ray absorptive cationic dye that can be excited by light energy having a wavelength in the range of 650 to 1500 nm. It is more desirable to use a boron-based sensitizer together.

The photo-acid generator may be a commonly-known photo-acid generator. Desirable examples of the photo-acid generator to be used in the present invention include sulfonic acid derivatives, onium salts, and carboxylic acid esters.

Examples of the sulfonic acid derivatives include disulfones, disulfonyldiazomethanes, disulfonylmethanes, sulfonylbenzoylmethanes, imidosulfonates such as trifluoromethylsulfonate derivatives, benzoin sulfonates, sulfonates of 1-oxy-2-hydroxy-3-propyl alcohol, pyrogallol trisulfonates, and benzyl sulfonates.

Specific examples thereof include diphenyldisulfone, ditosyldisulfone, bis(phenylsulfonyl)diazomethane, bis(chlorphenylsulfonyl)diazomethane, bis(xylylsulfonyl)diazomethane, phenylsulfonylbenzoyldiazomethane, bis(cyclohexylsulfonyl)methane, 1,8-naphthalenedicarboxylic acid imidomethylsulfonate, 1,8-naphthalenedicarboxylic acid imidotosylsulfonate, 1,8-naphthalenedicarboxylic acid imidotrifluoromethylsulfonate, 1,8-naphthalenedicarboxylic acid imidocamphorsulfonate, succinic acid imidophenylsulfonate, succinic acid imidotosylsulfonate, succinic acid imidotrifluoromethylsulfonate, succinic acid imidocamphorsulfonate, phthalic acid imidotrifluorosulfonate, cis-5-norbornene-endo-2,3-dicarboxylic acid imidotrifluoromethylsulfonate, benzoin tosylate, 1,2-diphenyl-2-hydroxypropyl tosylate, 1,2-di(4-methylmercaptophenyl)-2-hydroxypropyl tosylate, pyrogallol methylsulfonate, pyrogallol ethylsulfonate, 2,6-dinitrophenylmethyl tosylate, o-nitrophenylmethyl tosylate, and p-nitrophenyl tosylate.

Each of these may be used singly, or two or more of these may be used in combination. Similarly, carboxylic acid esters may be used in the present invention. Sulfonic acid derivatives and carboxylic acid esters are generally required to be heated (at 50° C.-100° C.) for releasing an acid.

Examples of the onium salts include sulfonium salts or iodonium salts having an anion such as tetrafluoroborate ($BF_4$—), hexafluorophosphate ($PF_6$—), hexafluoroantimonate ($SbF_6$—), hexafluoroarsenate ($AsF_6$—), hexachlorantimonate ($SbCl_6$—), tetraphenylborate, tetrakis(trifluoromethylphenyl)borate, tetrakis(pentafluoromethylphenyl)borate, perchlorate ion ($ClO_4$—), trifluoromethanesulfonate ion ($CF_3SO_3$—), fluorosulfonate ion ($FSO_3$—), toluenesulfonate ion, trinitrobenzenesulfonate anion, or trinitrotoluenesulfonate anion.

Examples of the sulfonium salts include triphenylsulfonium hexafluoroacylnate, triphenylsulfonium hexafluoroborate, triphenylsulfonium tetrafluoroborate, triphenylsulfonium tetrakis(pentafluorobenzyl)borate, methyldiphenylsulfonium tetrafluoroborate, methyldiphenylsulfonium tetrakis(pentafluorobenzyl)borate, dimethylphenylsulfonium hexafluorophosphate, triphenylsulfonium hexafluorophosphate, triphenylsulfonium hexafluoroantimonate, diphenylnaphthylsulfonium hexafluoroarsenate, tri-tolylsulfonium hexafluorophosphate, anisyldiphenylsulfonium hexafluorantimonate, 4-butoxyphenyldiphenylsulfonium tetrafluoroborate, 4-butoxyphenyldiphenylsulfonium tetrakis(pentafluorobenzyl)borate, 4-chlorophenyldiphenylsulfonium hexafluoroantimonate, tris(4-phenoxyphenyl)sulfonium hexafluorophosphate, di(4-ethoxyphenyl)methylsulfonium hexafluoroarsenate, 4-acetylphenyldiphenylsulfonium tetrafluoroborate, 4-acetylphenyldiphenylsulfonium tetrakis(pentafluorobenzyl)borate, tris(4-thiomethoxyphenyl)sulfonium hexafluorophosphate, di(methoxysulfonylphenyl)methylsulfonium hexafluoroantimonate, di(methoxynaphthyl)methylsulfonium tetrafluoroborate, di(methoxynaphthyl)methylsulfonium tetrakis(pentafluorobenzyl)borate, di(carbomethoxyphenyl)methylsulfonium hexafluorophosphate, (4-octyloxyphenyl)diphenylsulfonium tetrakis(3,5-bis-trifluoromethylphenyl)borate, tris(dodecylphenyl)sulfonium tetrakis(3,5-bis-trifluoromethylphenyl)borate, 4-acetamidophenyldiphenylsulfonium tetrafluoroborate, 4-acetamidophenyldiphenylsulfonium tetrakis(pentafluorobenzyl)borate, dimethylnaphthylsulfonium hexafluorophosphate, trifluoromethyldiphenylsulfonium tetrafluoroborate, trifluoromethyldiphenylsulfonium tetrakis(pentafluorobenzyl)borate, phenylmethylbenzylsulfonium hexafluorophosphate, 10-methylphenoxathiinium hexafluorophosphate, 5-methylthianthrenium hexafluorophosphate, 10-phenyl-9,9-dimethylthioxanthenium hexafluorophosphate, 10-phenyl-9-oxothioxanthenium tetrafluoroborate, 10-phenyl-9-oxothioxanthenium tetrakis(pentafluorobenzyl)borate, 5-methyl-10-oxothianthrenium tetrafluoroborate, 5-methyl-10-oxothianthrenium tetrakis(pentafluorobenzyl)borate, and 5-methyl-10,10-dioxothianthrenium hexafluorophosphate. Each of these may be used singly, or two or more of these may be used in combination.

Examples of the iodonium salts include (4-n-decyloxyphenyl)phenyliodonium hexafluoroantimonate, [4-(2-hydroxy-n-tetradecyloxy)phenyl]phenyliodonium hexafluoroantimonate, [4-(2-hydroxy-n-tetradecyloxy)phenyl] phenyliodonium trifluorosulfonate, [4-(2-hydroxy-n-tetradecyloxy)phenyl]phenyliodonium hexafluorophosphate, [4-(2-hydroxy-n-tetradecyloxy)phenyl]phenyliodonium tetrakis(pentafluorophenyl)borate, bis (4-t-butylphenyl)iodonium hexafluoroantimonate, bis(4-t-butylphenyl)iodonium hexafluorophosphate, bis(4-t-butylphenyl)iodonium trifluorosulfonate, bis(4-t-butylphenyl)iodonium tetrafluoroborate, bis(dodecylphenyl) iodonium hexafluoroantimonate, bis(dodecylphenyl) iodonium tetrafluoroborate, bis(dodecylphenyl)iodonium hexafluorophosphate, bis(dodecylphenyl)iodonium trifluoromethylsulfonate, di(dodecylphenyl)iodonium hexafluoroantimonate, di(dodecylphenyl)iodonium triflate, diphenyliodonium bisulfate, 4,4'-dichlorodiphenyliodonium bisulfate, 4,4'-dibromodiphenyliodonium bisulfate, 3,3'-dinitrodiphenyliodonium bisulfate, 4,4'-dimethyldiphenyliodonium bisulfate, 4,4'-bissuccinimidediphenyliodonium bisulfate, 3-nitrodiphenyliodonium bisulfate, 4,4'-dimethoxydiphenyliodonium bisulfate, bis(dodecylphenyl)iodonium tetrakis (pentafluorophenyl)borate, (4-octyloxyphenyl)phenyliodonium tetrakis(3,5-bis-trifluoromethylphenyl)borate; and (tolylcumyl)iodonium tetrakis(pentafluorophenyl)borate, $(CH_3C_6H_4)_2I$—$(SO_2CF_3)_3$, and $(C_6H_5)2I$-$B(C_6F_5)_4$ which are disclosed in U.S. Pat. No. 5,554,664. Each of these may be used singly, or two or more of these may be used in combination.

Aromatic diazonium salts may be also used as the onium salts, and an example thereof is p-methoxybenzenediazonium.hexafluoroantimonate.

Examples of the commercially available onium salts that can be used in the present invention include: San-Aid series SI-60, SI-80, SI-100, SI-60L, SI-80L, SI-100L, SI-L145, SI-L150, SI-L160, SI-L110, and SI-L147 (each produced by Sanshin Chemical Industry Co., Ltd.); UVI-6950, UVI-6970, UVI-6974, and UVI-6990 (each produced by Union Carbide Corp.) ADEKA OPTOMER series SP-150, SP-151, SP-170, SP-171, and SP-172 (each produced by ADEKA Corp.); Irgacure 261 (produced by Ciba Specialty Chemicals); CI-2481, CI-2624, CI-2639, and CI-2064 (each produced by Nippon Soda Co., Ltd.); CD-1010, CD-1011, and CD-1012 (each produced by Sartomer Company Inc.); DS-100, DS-101, DAM-101, DAM-102, DAM-105, DAM-201, DSM-301, NAI-100, NAI-101, NAI-105, NAI-106, SI-100, SI-101, SI-105, SI-106, PI-105, NDI-105, BENZOIN TOSYLATE, MBZ-101, MBZ-301, PYR-100, PYR-200, DNB-101, NB-101, NB-201, BBI-101, BBI-102, BBI-103, and BBI-109 (each produced by Midori Kagaku Co., Ltd.); PCI-061T, PCI-062T, PCI-020T, and PCI-022T (each produced by Nippon Kayaku Co., Ltd.); IBPF and IBCF (each produced by Sanwa Chemical Co., Ltd.); CD1012 (produced by Sartomer Company Inc.); IBPF and IBCF (each produced by Sanwa Chemical Co., Ltd.); BBI-101, BBI-102, BBI-103, and BBI-109 (each produced by Midori Kagaku Co., Ltd.); UVE1014 (produced by General Electric); and RHODORSIL-PI2074 (produced by Rhodia).

In addition, diaryliodonium salts produced by methods described in J. Polymer Science: Part A: polymer Chemistry, Vol. 31, 1473-1482 (1993) and J. Polymer Science: Part A: polymer Chemistry, Vol. 31, 1483-1491 (1993) may be used.

The photo-cationic initiator is not particularly limited as long as it generates cationic species or Lewis acid by active energy rays. The aforementioned photo-acid generator may be also used.

The photo-cationic initiator includes at least one of the following: metal fluoroboron complex salts and trifluoroboron complex compounds as disclosed in U.S. Pat. No. 3,379,653; bis(perfluoroalkylsulfonyl)methane metal salts as disclosed in U.S. Pat. No. 3,586,616; aryldiazonium compounds as disclosed in U.S. Pat. No. 3,708,296; aromatic onium salts of VIa group elements as disclosed in U.S. Pat. No. 4,058,400; aromatic onium salts of Va group elements as disclosed in U.S. Pat. No. 4,069,055; dicarbonyl chelates of IIIa to Va group elements as disclosed in U.S. Pat. No. 4,068,091; thiopyrylium salts as disclosed in U.S. Pat. No. 4,139,655; VIb elements in the form of $MF_6^-$ anion (wherein M represents phosphorous, antimony, or arsenic) as disclosed in U.S. Pat. No. 4,161,478; arylsulfonium complex salts as disclosed in U.S. Pat. No. 4,231,951; aromatic iodonium complex salts and aromatic sulfonium complex salts as disclosed in U.S. Pat. No. 4,256,828; bis[4-(diphenylsulfonio)phenyl]sulfide-bis-hexafluoro metal salts (such as phosphates, arsenates, and antimonates) as described in Journal of Polymer Science: Polymer Chemistry, Vol. 22, 1789 (1984); and aromatic iodonium complex salts and aromatic sulfonium complex salts each having an anion B $(C_6F_5)_4^-$.

Desirable cation type photo-cationic initiators include arylsulfonium complex salts, aromatic sulfonium or iodonium salts of halogen-containing complex ions, and aromatic onium salts of II group, V group, and VI group elements. Some of these salts may be commercially available as FX-512 (produced by 3M Company), UVR-6990 and UVR-6974 (each produced by Union Carbide Corp.), UVE-1014 and UVE-1016 (each produced by General Electric), KI-85 (produced by Degussa), SP-152 and SP-172 (each produced by ADEKA Corp.), San-Aid series SI-60L, SI-80L and SI-100L (each produced by Sanshin Chemical Industry Co., Ltd.), WPI113 and WPI116 (each produced by Wako Pure Chemical Industries, Ltd.), and RHODORSIL PI2074 (produced by Rhodia).

The amount of the curing initiator in the composition of the present invention is not particularly limited. It is desirably 0.01 to 10 parts by weight per 100 parts by weight of the modified polyhedral polysiloxane from the viewpoint of curability. It is more desirably 0.05 to 5.0 parts by weight from the viewpoint of the balance of physical properties of a cured product.

A smaller amount of the curing initiator may result in longer curing time period or failure to provide a sufficiently cured product. A larger amount of the curing initiator may problematically lead to residue of its color in a cured product or to staining and poor heat and light resistances due to rapid curing.

The composition containing the photo-curing initiator of the present invention may further contain a sensitizer for promoting release of active species. The sensitizer is not particularly limited, and widely known ones may be used. The amount of the sensitizer is not particularly limited. It is desirably 0.01 to 10 parts by weight, and more desirably 0.02 to 5 parts by weight, per 100 parts by weight of the modified polyhedral polysiloxane.

The composition of the present invention containing the photo-curing initiator is allowed to cure by irradiation of active energy rays, is allowed to cure at very high speed, and can achieve a reduction in the thermal history. The intensity and irradiation time period of the active energy rays may be set depending on applications and production steps. In the case where the curing reaction insufficiently proceeds only by irradiation of the active energy rays, the curing reaction may be allowed to further proceed by the subsequent annealing.

<Curing Agent>

Next, the curing agent to be used in the present invention will be described below.

The curing agent may be selected depending on the kind of a main reactive functional group of the modified polyhedral polysiloxane. In the case where the main reactive functional group of the modified polyhedral polysiloxane is a hydrosilyl group, an alkenyl group-containing compound may be used as the curing agent; while in the case where the main reactive functional group of the modified polyhedral polysiloxane is an alkenyl group, a hydrosilyl group-containing compound may be used as the curing agent. This will be specifically described below.

The alkenyl group-containing curing agent is not particularly limited as long as it is an alkenyl group-containing compound. It desirably contains at least two alkenyl groups in the molecule. Particularly desirable are siloxane compounds such as alkenyl group-containing linear polysiloxanes, polysiloxanes having alkenyl groups at the molecular ends, and alkenyl group-containing cyclic siloxanes. Each of these alkenyl group-containing compounds may be used singly, or two or more may be used in combination.

An alkenyl group-containing polysiloxane having a molecular weight less than 3000 and an alkenyl group-containing polysiloxane having a molecular weight of 5000 or more may be used together as the alkenyl group-containing compound. The molecular weight can be determined by the GPC method on the polystyrene equivalent basis.

The alkenyl group-containing polysiloxane having a molecular weight less than 3000 is not particularly limited as long as it contains at least one alkenyl group in the molecule and is a polysiloxane having a molecular weight less than 3000.

According to the present invention, the alkenyl group-containing polysiloxane having a molecular weight less than 3000 desirably contains at least two alkenyl groups in the molecule. Desirable examples thereof include alkenyl group-containing polysiloxanes such as alkenyl group-containing linear polysiloxanes, polysiloxanes having alkenyl groups at the molecular end, and alkenyl group-containing cyclic siloxanes from the viewpoints of heat and light resistances.

The substituent group other than the alkenyl group in the alkenyl group-containing polysiloxane having a molecular weight less than 3000 of the present invention is desirably a methyl group or a hydrogen atom from the viewpoints of further improved heat and light resistances. Each of these alkenyl group-containing polysiloxanes may be used singly, or two or more of these may be used in combination.

Specific examples of the alkenyl group-containing linear polysiloxanes include: copolymers of a dimethylsiloxane unit, a methylvinylsiloxane unit, and a terminal trimethylsiloxy unit; copolymers of a diphenylsiloxane unit, a methylvinylsiloxane unit, and a terminal trimethylsiloxy unit; copolymers of a methylphenylsiloxane unit, a methylvinylsiloxane unit, and a terminal trimethylsiloxy unit; polydimethylsiloxanes with each end terminated by a dimethylvinylsilyl group; polydiphenylsiloxanes with each end terminated by a dimethylvinylsilyl group; and polymethylphenylsiloxanes with each end terminated by a dimethylvinylsilyl group.

Specific examples of the polysiloxanes having alkenyl groups at the molecular ends include: the above-exemplified polysiloxanes with each end terminated by a dimethylalkenyl group; and polysiloxanes comprising a dimethylalkenylsiloxane unit and at least one siloxane unit selected from the group consisting of a $SiO_2$ unit, a $SiO_{3/2}$ unit and a SiO unit.

Examples of the alkenyl group-containing cyclic siloxane compounds include 1,3,5,7-tetravinyl-1,3,5,7-tetramethylcyclotetrasiloxane, 1-propyl-3,5,7-trivinyl-1,3,5,7-tetramethylcyclotetrasiloxane, 1,5-divinyl-3,7-dihexyl-1,3,5,7-tetramethylcyclotetrasiloxane, 1,3,5-trivinyl-trimethylcyclosiloxane, 1,3,5,7,9-pentavinyl-1,3,5,7,9-pentamethylcyclosiloxane, and 1,3,5,7,9,11-hexavinyl-1,3,5,7,9,11-hexamethylcyclosiloxane.

According to the present invention, the alkenyl group-containing polysiloxane having a molecular weight of 5000 or more is not particularly limited as long as it contains at least one alkenyl group in the molecule and is a polysiloxane having a molecular weight of 5000 or more.

The alkenyl group-containing polysiloxane having a molecular weight of 5000 or more is desirably a polysiloxane having an alkenyl group at the molecular end for reducing stress generated by curing shrinkage or thermal expansion/shrinkage upon curing. It is more desirably a linear polysiloxane having an alkenyl group at the molecular end.

The polysiloxane of the alkenyl group-containing polysiloxane having a molecular weight of 5000 or more of the present invention is desirably polydimethylsiloxane from the viewpoints of heat and light resistances. Each of the alkenyl group-containing polysiloxanes having a molecular weight of 5000 or more may be used singly, or two or more of these may be used in combination.

According to the present invention, with respect to the content ratio of the alkenyl group-containing polysiloxane having a molecular weight less than 3000 and the alkenyl group-containing polysiloxane having a molecular weight of 5000 or more, the content ratio of the alkenyl group-containing polysiloxane having a molecular weight less than 3000 is desirably 50 to 99% by weight, and more desirably 60 to 95% by weight, to the total amount (100% by weight) of both of the polysiloxanes.

A larger amount of the alkenyl group-containing polysiloxane having a molecular weight less than 3000 may cause insufficient reduction in stress. Specifically, this may result in, for example, warpage of a substrate, separation from a substrate, or cracks due to curing shrinkage or thermal expansion/shrinkage upon curing. A smaller amount of the polysiloxane may cause too much reduction in elastic modulus.

The hydrosilyl group-containing curing agent is not particularly limited as long as it is a hydrosilyl group-containing compound. It desirably contains at least two hydrosilyl groups in the molecule. Particularly desirable are siloxane compounds such as hydrosilyl group-containing linear polysiloxanes, polysiloxanes having hydrosilyl groups at the molecular ends, and hydrosilyl group-containing cyclic siloxanes. Each of these hydrosilyl group-containing compounds may be used singly, or two or more of these may be used in combination.

Specific examples of the hydrosilyl group-containing linear polysiloxanes include: copolymers of a dimethylsiloxane unit, a methylhydrogensiloxane unit, and a terminal trimethylsiloxy unit; copolymers of a diphenylsiloxane unit, a methylhydrogensiloxane unit, and a terminal trimethylsiloxy unit; copolymers of a methylphenylsiloxane unit, a methylhydrogensiloxane unit, and a terminal trimethylsiloxy unit; polydimethylsiloxanes with each end terminated by a dimethylhydrogensilyl group; polydiphenylsiloxanes with each end terminated by a dimethylhydrogensilyl group; and polymethylphenylsiloxanes with each end terminated by a dimethylhydrogensilyl group.

Examples of the polysiloxanes having hydrosilyl groups at the molecular ends include: the above-exemplified polysiloxanes with each end terminated by a dimethylhydrogensilyl group; and polysiloxanes comprising a dimethylhydrogensiloxane unit ($H(CH_3)_2SiO_{1/2}$ unit) and at least one siloxane unit selected from the group consisting of a $SiO_2$ unit, a $SiO_{3/2}$ unit and a SiO unit.

Examples of the hydrosilyl group-containing cyclic siloxane compounds include 1,3,5,7-tetrahydrogen-1,3,5,7-tetramethylcyclotetrasiloxane, 1-propyl-3,5,7-trihydrogen-1,3,5,7-tetramethylcyclotetrasiloxane, 1,5-dihydrogen-3,7-dihexyl-1,3,5,7-tetramethylcyclotetrasiloxane, 1,3,5-trihydrogen-trimethylcyclosiloxane, 1,3,5,7,9-pentahydrogen-1,3,5,7,9-pentamethylcyclosiloxane, and 1,3,5,7,9,11-hexahydrogen-1,3,5,7,9,11-hexamethylcyclosiloxane.

In the present invention, groups on the Si atoms desirably comprise a hydrogen atom, a vinyl group, and a methyl group from the viewpoints of heat and light resistances.

The amount of the curing agent is optionally determined. The curing agent is desirably used in such an amount that the number of a hydrogen atom directly bonded to a Si atom is 0.3 to 5, desirably 0.5 to 3 per one alkenyl group. A smaller amount of the alkenyl group tends to cause poor appearance due to foaming or other problems. A larger amount of the alkenyl group may have a bad influence on physical properties of a cured product.

<Curing Retardant>

Next, the curing retardant to be used in the present invention will be described below.

The curing retardant improves storage stability of the modified polyhedral polysiloxane and the polysiloxane composition of the present invention, or controls reactivity of the hydrosilylation reaction in the curing step. In the present invention, commonly-known curing retardants used for compositions that are addition-curable by hydrosilylation catalysts may be used as the curing retardant. Specific examples thereof include aliphatic unsaturated bond-containing compounds, organophosphorous compounds, organosulfur compounds, nitrogen-containing compounds, tin compounds, and organoperoxides. Each of these may be used singly, or two or more of these may be used in combination.

Specific examples of the aliphatic unsaturated bond-containing compounds include: propargyl alcohols such as 3-hydroxy-3-methyl-1-butyne, 3-hydroxy-3-phenyl-1-butyne, 3,5-dimethyl-1-hexyn-3-ol, and 1-ethynyl-1-cyclohexanol; ene-yne compounds; and maleates such as maleic anhydrides and dimethyl maleate.

Specific examples of the organophosphorous compounds include triorganophosphines, diorganophosphines, organophosphones, and triorganophosphites.

Specific examples of the organosulfur compounds include organomercaptans, diorganosulfides, hydrogen sulfide, benzothiazole, thiazole, and benzothiazole disulfide.

Specific examples of the nitrogen-containing compounds include N,N,N',N'-tetramethylethylenediamine, N,N-dimethylethylenediamine, N,N-diethylethylenediamine, N,N-dibutylethylenediamine, N,N-dibutyl-1,3-propanediamine, N,N-dimethyl-1,3-propanediamine, N,N,N',N'-tetraethylethylenediamine, N,N-dibutyl-1,4-butanediamine, and 2,2'-bipyridine.

Specific examples of the tin compounds include stannous halide dihydrates and stannous carboxylates.

Specific examples of the organoperoxides include di-t-butylperoxide, dicumylperoxide, benzoylperoxide, and t-butyl perbenzoate.

Particularly desirable among these curing retardants are dimethyl maleate, 3,5-dimethyl-1-hexyn-3-ol, and 1-ethynyl-1-cyclohexanol.

The amount of the curing retardant is not particularly limited. The curing retardant may be desirably used in an amount of $10^{-1}$ to $10^3$ mol, and more desirably 1 to 500 mol, per 1 mol of the hydrosilylation catalyst. Each of these curing retardants may be used singly, or two or more of these may be used in combination.

<Adhesion Promoter>

The adhesion promoter is used for the purpose of increasing adhesiveness between the composition of the present invention and a substrate. The adhesion promoter is not particularly limited as long as it has such an effect. Desirable examples thereof include silane coupling agents and epoxy compounds.

Specifically, for example, a cured product that is favorable in adhesiveness to a substrate can be provided from the composition produced by adding the curing agent, the hydrosilylation catalyst, and the adhesion promoter to the hydrosilyl group-containing modified polyhedral polysiloxane as the modified polyhedral polysiloxane.

The silane coupling agent is not particularly limited as long as it has at least one functional group reactive with an organic group and at least one hydrolyzable silicon group in the molecule. The functional group reactive with an organic group is desirably at least one functional group selected from the group consisting of an epoxy group, a methacryl group, an acryl group, an isocyanate group, an isocyanurate group, a vinyl group, and a carbamate group from the viewpoint of handleability. It is particularly desirably an epoxy group, a methacryl group, or an acryl group from the viewpoints of curability and adhesiveness. The hydrolyzable silicon group is desirably an alkoxysilyl group from the viewpoint of handleability, and is particularly desirably a methoxysilyl group or an ethoxysilyl group from the viewpoint of reactivity.

Specific examples of the desirable silane coupling agent include: epoxy group-containing alkoxysilanes such as 3-glycidoxypropyltrimethoxysilane, 3-glycidoxypropyltriethoxysilane, 2-(3,4-epoxycyclohexyl)ethyltrimethoxysilane, and 2-(3,4-epoxycyclohexyl)ethyltriethoxysilane; and methacryl group- or acryl group-containing alkoxysilanes such as 3-methacryloxypropyltrimethoxysilane, 3-methacryloxypropyltriethoxysilane, 3-acryloxypropyltrimethoxysilane, 3-acryloxypropyltriethoxysilane, methacryloxymethyltrimethoxysilane, methacryloxymethyltriethoxysilane, acryloxymethyltrimethoxysilane, and acryloxymethyltriethoxysilane.

The amount of the silane coupling agent is desirably 0.05 to 30% by weight, and more desirably 0.1 to 15% by weight, to the total amount of the modified polyhedral polysiloxane and the curing agent. A smaller amount of the silane coupling agent may fail to increase adhesiveness, and a larger amount of the silane coupling agent may have a bad influence on physical properties of a cured product.

Examples of the epoxy compound include novolac phenol epoxy resin, biphenyl epoxy resin, dicyclopentadiene epoxy resin, bisphenol F diglycidyl ether, bisphenol A diglycidyl ether, 2,2'-bis(4-glycidyloxycyclohexyl)propane, 3,4-epoxycyclohexylmethyl-3,4-epoxycyclohexane carboxylate, 2-(3,4-epoxycyclohexyl)-5,5-spiro-(3,4-epoxycyclohexane)-1,3-dioxane, bis(3,4-epoxycyclohexyl)adipate, 1,2-cyclopropanedicarboxylic acid bisglycidyl ester, and triglycidylisocyanurate.

The amount of the epoxy compound is desirably 0.1 to 50% by weight, and more desirably 0.2 to 15% by weight, to the total amount of the modified polyhedral polysiloxane and the curing agent. A smaller amount of the epoxy compound may fail to increase adhesiveness, and a larger amount thereof may have a bad influence on physical properties of a cured product.

Each of the silane coupling agents and epoxy compounds may be used singly, or two or more of these may be used in combination.

In the present invention, a commonly-known adhesiveness promoter may be used for the purpose of enhancing effects of the adhesion promoter. Examples of the adhesiveness promoter include, but are not limited to, boronate ester compounds, organoaluminum compounds, and organotitanium compounds.

In addition to the aforementioned ingredients, the polysiloxane composition according to the present invention may contain, if necessary, an inorganic filler such as crushed quartz, calcium carbonate, carbon black, or silica, to the extent that these ingredients do not inhibit the effects of the present invention.

<Inorganic Filler>

The inorganic filler to be used in the present invention is not particularly limited as long as it is an inorganic substance or a compound containing an inorganic substance. Specific examples thereof include silica-type inorganic fillers such as quartz, fumed silica, precipitated silica, silicic anhydride, fused silica, crystalline silica, and ultra-fine amorphous silica, alumina, zircon, iron oxide, zinc oxide, titanium oxide, silicon nitride, boron nitride, aluminum nitride, silicon carbide, glass fibers, glass flakes, alumina fibers, carbon fibers, mica, black lead, carbon black, ferrite, graphite, diatomaceous earth, kaolin, clay, talc, aluminum hydroxide, calcium carbonate, manganese carbonate, magnesium carbonate, barium sulfate, potassium titanate, calcium silicate, inorganic balloons, and silver powder. Each of these may be used singly, or two or more of these may be used in combination.

The inorganic filler may be optionally subjected to surface treatment. Examples of the surface treatment include, but are not limited to, alkylation, trimethylsilylation, siliconization, and treatment with a coupling agent.

An example of the coupling agent is a silane coupling agent. The silane coupling agent is not particularly limited as long as it has at least one functional group reactive with an organic group and at least one hydrolyzable silicon group in the molecule. The functional group reactive with an organic group is desirably at least one functional group selected from the group consisting of an epoxy group, a methacryl group, an acryl group, an isocyanate group, an isocyanurate group, a vinyl group, and a carbamate group from the viewpoint of handleability. It is particularly desirably an epoxy group, a methacryl group, or an acryl group from the viewpoints of curability and adhesiveness. The hydrolyzable silicon group is desirably an alkoxysilyl group from the viewpoint of handleability, and is particularly desirably a methoxysilyl group or an ethoxysilyl group from the viewpoint of reactivity.

Examples of the desirable silane coupling agent include: epoxy group-containing alkoxysilanes such as 3-glycidoxypropyltrimethoxysilane, 3-glycidoxypropyltriethoxysilane, 2-(3,4-epoxycyclohexyl)ethyltrimethoxysilane, and 2-(3,4-epoxycyclohexyl)ethyltriethoxysilane; and methacryl group- or acryl group-containing alkoxysilanes such as 3-methacryloxypropyltrimethoxysilane, 3-methacryloxypropyltriethoxysilane, 3-acryloxypropyltrimethoxysilane, 3-acryloxypropyltriethoxysilane, methacryloxymethyltrimethoxysilane, methacryloxymethyltriethoxysilane, acryloxymethyltrimethoxysilane, and acryloxymethyltriethoxysilane.

The polysiloxane composition containing the inorganic filler as an ingredient can provide a molded product having improved physical properties such as strength, hardness, elastic modulus, coefficient of thermal expansion, thermal conductivity, heat dissipation, electrical properties, light reflectivity, flame retardancy, and fire resistance.

The inorganic filler may be used in any shape such as a crushed shape, a flake shape, a spherical shape, or a bar-like shape. The average particle size and the particle size distribution of the inorganic filler are not particularly limited. The average particle size is desirably 0.005 to 100 μm, and more desirably 0.01 to 50 μm. The specific surface area thereof is also not particularly limited.

The amount of the inorganic filler is not particularly limited. The amount thereof is 1 to 1000 parts by weight, more desirably 5 to 500 parts by weight, and furthermore desirably 10 to 300 parts by weight, per 100 parts by weight of the mixture of the modified polyhedral polysiloxane and the curing agent. A larger amount of the inorganic filler may cause poor fluidity. A smaller amount of the inorganic filler may cause insufficient physical properties of a molded product to be provided.

The composition according to the present invention may be provided by adding the inorganic filler to the modified polyhedral polysiloxane of the present invention and the curing agent. Here, the modified polyhedral polysiloxane is desirably one provided by modifying the alkenyl group-containing polyhedral polysiloxane compound (a) with the hydrosilyl group-containing compound (b).

The mixing order of the inorganic filler is not particularly limited. For achieving good storage stability, it is desirable that the inorganic filler and the curing agent are mixed with each other, and then the modified polyhedral polysiloxane is mixed therewith. For providing a stable molded product in which the modified polyhedral polysiloxane and the curing agent are well-mixed, it is desirable that the modified polyhedral polysiloxane and the curing agent are mixed with each other, and then the inorganic filler is mixed therewith.

The means of mixing the inorganic filler is not particularly limited. Specific examples of the means include stirring apparatuses such as a two-roll or three-roll mill, a planetary stirring and defoaming apparatus, a homogenizer, a dissolver, and a planetary mixer, and a melt-kneading apparatuses such as a plast mill. The inorganic filler may be mixed at normal temperature or under heated condition, and also may be mixed at normal pressure or under vacuum condition. If mixing is performed at high temperatures, the composition may be problematically cured before molding. Furthermore, the polysiloxane composition of the present invention may optionally contain various additives such as a pigment, a phosphor, a coloring agent, and a heat-resistance improver, a reaction regulator, a release agent, and a dispersant for fillers, if necessary.

Examples of the dispersant for fillers include diphenylsilanediol, alkoxysilanes, carbon-functional silanes, and silanol group-containing siloxanes with low molecular weight.

In order to impart flame retardancy and fire resistance to the polysiloxane composition of the present invention, a commonly-known additive such as titanium dioxide, manganese carbonate, $Fe_2O_3$, ferrite, mica, glass fibers, or glass flakes may be added. The amount of such an optional ingredient is desirably as low as possible so as not to inhibit the effects of the present invention.

The polysiloxane composition of the present invention may be provided by uniformly mixing the aforementioned ingredients with a kneading apparatus such as a roll mill, a Banbury mixer, or a kneader, or with a planetary stirring and defoaming apparatus and then, if necessary, heating the mixture.

The polysiloxane composition of the present invention may be used as a molding material. The composition may be molded by any method, such as extrusion molding, compression molding, blow molding, calender molding, vacuum forming, foam molding, injection molding, liquid injection molding, and cast molding. The polysiloxane composition of the present invention may be applied to a substrate such as silicon material or glass by a spin coater or other like coaters to form a coating. At this time, the composition may be diluted by any solvent so as to control the viscosity.

Furthermore, introduction of an alkali-soluble group such as an organic acid functional group, which involves decreases in heat and light resistances, is not required, so that cured products from the composition of the present invention can be used at high temperatures and under strong light exposure.

The cured product from the polysiloxane composition of the present invention has excellent heat and light resistances, and exerts high transparency at a wide range of wavelengths and temperatures. The cured product may be also suitably used as a material having low-dielectric properties and a low refractive index.

The cured product, molded product, and film produced from the polysiloxane composition of the present invention have excellent heat and light resistances, and are highly transparent even to ultraviolet rays having a wavelength of about 400 nm. Such properties allow these products to be used as materials for optical devices (optical materials).

The polysiloxane composition of the present invention may be used as a composition for an optical material. The composition may be subjected to curing or the like and therefore used as, for example, a material for optical devices.

The optical material used herein means a general material through which lights such as visible lights, infrared rays, ultraviolet rays, X-rays, or lasers, are transmitted. In order to use as an optical material, the light transmittance of the cured product having a thickness of 3 mm at a wavelength of 400 nm is desirably 70% or more, and more desirably 75% or more. Currently, optical materials are required to have high heat and light resistances and, in particular, the optical materials should exhibit a small decrease in the light transmittance after the tests (desirably, the decreasing rate of the light transmittance is 5% or less of the light transmittance before the tests).

The cured product provided according to the present invention is excellent in durability against laser lights having shorter wavelengths (350 to 450 nm). For example, it is possible that the laser-light transmittance changes only slightly even in the case of a long-time irradiation of blue-violet laser of 405±10 nm. Accordingly, in the case of using the cured product as a material for optical devices, the cured product allows the device to be used for a long time.

Specifically, for example, the gel fraction is desirably 95% or more for achieving high durability against lasers having shorter wavelengths. If the gel fraction is less than 95%, a laser-transmitting part may have a change in the refractive index, have stripes, or have irregularities on the surface.

The gel fraction is specifically determined as follows: for example, 1 g of a sample is wrapped in a stainless-steel wire gauze, and then immersed in toluene for 72 hours at 20±5° C.; next, the sample is dried at 100° C. for 5 hours; and thereby, the gel fraction is determined from the sample weights before and after the test. Specifically, the gel fraction can be determined by the following calculating formula.

(Gel fraction)=[(Weight after test)/(Weight before test)]×100

Specific examples of applications of the polysiloxane composition and the molded product provided by the present invention include: peripheral materials for liquid crystal displays in the liquid crystal display field, such as color filters, resist materials, substrate materials, light guide plates, prism sheets, polarizing plates, phase plates, viewing angle compensation films, adhesives, polarizer protective films, films for liquid crystal displays, interlayer insulators, gate insulators, and passivation films.

Examples of the applications further include: materials for color PDPs (plasma display panels) which are expected to be the next generation flat panel displays, such as encapsulants, antireflection coatings, antireflection films, optical compensation films, housing materials, films for protecting front glass, substitution materials for front glass, and adhesives.

Examples of the applications further include: materials for plasma address liquid crystal (PALC) displays, such as substrate materials, light guide plates, prism sheets, polarizing plates, phase plates, viewing angle compensation films, adhesives, encapsulants, and polarizer protective films.

Examples of the applications further include: materials for organic electro-luminescence (EL) displays, such as films for protecting front glass, substitution materials for front glass, encapsulants, and adhesives; and materials for field emission displays (FEDs), such as film substrates, films for protecting front glass, substitution materials for front glass, and adhesives.

Examples of the applications further include: materials for LED displays, such as molding materials for LED elements, films for protecting front glass, substitution materials for front glass, and adhesives.

Examples of the applications in the optical recording field include disk substrate materials, pickup lenses, protective films, encapsulants, and adhesives for VD (video disk), CD/CD-ROM, CD-R/RW, DVD-R/DVD-RAM, MO/MD, PD (phase change disk), and optical memory cards. More specifically, suitable examples thereof include materials for optical pickups of the next generation DVDs, such as pickup lenses, collimator lenses, objective lenses, sensor lenses, protective films, encapsulants for elements, encapsulants for sensors, gratings, adhesives, prisms, wavelength plates, compensation plates, splitters, holograms, and mirrors.

Examples of the applications in the optical device field include: materials for still cameras, such as lens materials, finder prisms, target prisms, finder covers, and light receiving sensors; materials for video cameras, such as taking lenses and finders; materials for projection televisions, such as projection lenses, protective films, encapsulants, and adhesives; and materials for light sensing devices, such as lens materials, encapsulants, adhesives, and films.

Examples of the applications in the optical component field include: peripheral materials for optical switches in optical communication systems, such as fiber materials, lenses, waveguides, encapsulants for elements, and adhesives; peripheral materials for optical connectors, such as optical fiber materials, ferrules, encapsulants, and adhesives; materials for optical passive components and light circuits, such as lenses, waveguides, encapsulants for LED elements, and adhesives; and peripheral materials for optoelectronic integrated circuits (OEIC), such as substrate materials, fiber materials, element encapsulants, and adhesives.

Examples of the applications in the optical fiber field include: lightings for decorative display and light guides; industrial sensors, indications, and signs; and optical fibers for communication infrastructures and for connecting household digital devices.

Examples of the applications include peripheral materials for semiconductor integrated circuits, such as microlithography resist materials for LSI and VLSI materials.

Examples of the applications in the automobile and transportation fields include: materials for automobiles, such as lamp reflectors, bearing retainers, gear parts, corrosion-resist coatings, switch parts, headlamps, engine inner parts, electrical parts, interior and exterior parts, driving engines, brake-oil tanks, rustproof steel plates, interior panels, interior materials, protecting/binding wire harnesses, fuel hoses, lamps, and glass substitutions;

materials for railway vehicles, such as multilayer glasses; and materials for aircrafts, such as tenacity-imparting agents to structural materials, engine peripheral materials, protecting/binding wire harnesses, and corrosion-resist coatings.

Examples of the applications in the architecture field include interior/processing materials, lamp covers, sheets, glass interlayer films, glass substitutions, and peripheral materials for solar cells. Examples of the applications in the agricultural field include cover films for greenhouses.

Examples of the applications include the next generation optical/electronic functional organic materials such as peripheral materials for the next generation DVDs, organic EL element peripheral materials, organic photorefractive elements, light amplifying elements which are light-to-light conversion devices, optical computing elements, substrate materials for peripheral components of organic solar cells, fiber materials, encapsulants for elements, and adhesives.

The composition containing the modified polyhedral polysiloxane of the present invention can be suitably used as an encapsulant for optical elements, a composition for optical elements, and an insulator. Said modified polyhedral polysiloxane is desirably the modified polyhedral polysiloxane produced by modifying an alkenyl group-containing polyhedral polysiloxane compound (a) with a hydrosilyl group-containing compound (b) according to the present invention.

Similarly, the polysiloxane composition of the present invention can be suitably used as an encapsulant for optical elements, a composition for optical elements, and an insulator.

Each of the encapsulant for optical elements, the composition for optical elements, and the insulator is also one aspect of the present invention.

<Encapsulant for Optical Elements>

The encapsulant for optical elements of the present invention may be provided by adding a curing agent and, if necessary, a hydrosilylation catalyst, a curing retardant, and an adhesion promoter, to the modified polyhedral polysiloxane. The encapsulant for optical elements of the present invention may be formed into a transparent liquid resin composition. In the case of the liquid composition, it is easy to seal an element by pouring the encapsulant into a mold, a package, or onto a substrate and then curing the encapsulant by heat. A sealing layer formed from the encapsulant for optical elements of the present invention has high transparency, and thereby it is suitably used from the viewpoint of light extraction efficiency. It also has excellent heat, light, and blue-violet-laser resistances, so that it allows optical devices to be used for a long time.

For example, a cured product of the liquid encapsulant for optical elements may have a light transmittance of 75% or more at a wavelength of 400 nm when it has a thickness of 3 mm. The modified polyhedral polysiloxane is desirably in a liquid state so as to easily provide the encapsulant for optical elements in a liquid state.

In the case of heating the encapsulant upon curing, the curing temperature is desirably 30° C. to 400° C., and more desirably 50° C. to 250° C. A higher curing temperature tends to cause poor appearance on a cured product to be provided, and a lower curing temperature may cause insufficient curing. Curing may be performed using combinations between two or more temperature conditions. Specifically, the curing temperature is desirably stepwise increased, for example, to 70° C., then to 120° C., and finally to 150° C., because such increase makes it possible to provide a favorable cured product.

In the present invention, a hydrosilylation catalyst may be added if necessary. The curing time period may be set depending on the curing temperature, the amounts of a hydrosilylation catalyst to be used and a hydrosilyl group, and the combination of other ingredients of the present composition. For example, a favorable cured product may be provided by a curing reaction for 1 minute to 12 hours, and desirably for 10 minutes to 8 hours.

Specifically, for example, the encapsulant for optical elements of the present invention may be cast or applied to a package or a substrate on which an element is mounted. Curing under the aforementioned curing conditions after the casting or application can provide favorable element sealing.

To the encapsulant for optical elements of the present invention may be added, in addition to the above essential ingredients, fillers such as silica, crushed quartz, calcium carbonate, carbon black, titanium oxide, zinc oxide, alumina, and phosphors as optional ingredients to the extent that these ingredients do not inhibit the effects of the present invention.

To the encapsulant for optical elements may be optionally added additives such as a coloring agent and a heat-resistance improver, a reaction regulator, a release agent, and a dispersant for fillers, if necessary.

Examples of the dispersant for fillers include diphenylsilanediol, alkoxysilanes, carbon-functional silanes, and silanol group-containing siloxanes with low molecular weight.

In order to impart flame retardancy and fire resistance to the encapsulant for optical elements of the present invention, a commonly-known additive such as titanium dioxide, manganese carbonate, $Fe_2O_3$, ferrite, mica, glass fibers, or glass flakes may be added. The amount of such an optional ingredient is desirably as low as possible so as not to inhibit the effects of the present invention.

The encapsulant for optical elements of the present invention may be provided by uniformly mixing the aforementioned ingredients with a kneading apparatus such as a roll mill, a Banbury mixer, or a kneader, or with a planetary stirring and defoaming apparatus and then, if necessary, heating the mixture.

The encapsulant for optical elements of the present invention may be used as a molding material. The encapsulant may be molded by any method, such as extrusion molding, compression molding, blow molding, calender molding, vacuum forming, foam molding, injection molding, liquid injection molding, and cast molding.

A cured product (sealing layer) from the encapsulant for optical elements of the present invention has excellent heat, light and blue-violet-laser resistances. The cured product also has high light transmittance even to near-ultraviolet rays having a wavelength of about 400 nm.

<Composition for Optical Elements and Optical Element>

The composition for optical elements of the present invention may be provided by adding a curing agent and, if necessary, a hydrosilylation catalyst, a curing retardant, and an adhesion promoter, to the modified polyhedral polysiloxane.

The composition for optical elements of the present invention may be formed into a transparent liquid resin composition. In the case of the liquid composition, it is easy to produce an optical element by, for example, injecting or casting the composition into a mold and then curing the composition by heat.

An optical element provided using the composition for optical elements of the present invention has high transparency, and thereby it is suitably used from the viewpoint of light extraction efficiency. It also has excellent heat, light, and blue-violet-laser resistances, so that it can inhibit reduction in product quality due to the thermal history upon optical-device production, and it allows optical devices to be used for a long time.

For example, a cured product (optical element) from the liquid composition for optical elements may have a light transmittance of 75% or more at a wavelength of 400 nm when it has a thickness of 3 mm. The modified polyhedral polysiloxane is desirably in a liquid state so as to easily provide the composition for optical elements in a liquid state.

In the case of heating the composition upon curing, the curing temperature is desirably 30° C. to 400° C., and more desirably 50° C. to 250° C. A higher curing temperature tends to cause poor appearance on a cured product to be provided, and a lower curing temperature may cause insufficient curing. Curing may be performed using combinations between two or more temperature conditions. Specifically, the curing temperature is desirably stepwise increased, for example, to 70° C., then to 120° C., and finally to 150° C., because such increase makes it possible to provide a favorable cured product.

In the present invention, a hydrosilylation catalyst may be added if necessary. The curing time period may be set depending on the curing temperature, the amounts of a hydrosilylation catalyst to be used and a hydrosilyl group, and the combination of other ingredients of the present composition. For example, a favorable cured product may be provided by a curing reaction for 1 minute to 12 hours, and desirably for 10 minutes to 8 hours.

Specifically, for example, the composition for optical elements of the present invention may be provided by injecting or casting the composition into a mold for an optical element and then curing the composition. Alternatively, an optical element may be provided as a composite material by applying the composition to a substrate for optical elements made of glasses, plastics or the like and then curing the composition. In the case where a mold with fine grooves, holes and/or dots is pushed against the composition applied on the substrate during curing, an optical element having such fine structures on the surface may be provided.

The composition for optical elements of the present invention can impart antireflection properties to optical elements made of glasses, plastics or the like.

To the composition for optical elements of the present invention may be added, in addition to the above essential ingredients, fillers such as silica, crushed quartz, calcium carbonate, carbon black, titanium oxide, zinc oxide, alumina, and phosphors as optional ingredients to the extent that these ingredients do not inhibit the effects of the present invention.

To the composition for optical elements may be optionally added additives such as a coloring agent and a heat-resistance improver, a reaction regulator, a release agent, and a dispersant for fillers, if necessary.

Examples of the dispersant for fillers include diphenylsilanediol, alkoxysilanes, carbon-functional silanes, and silanol group-containing siloxanes with low molecular weight.

In order to impart flame retardancy and fire resistance to the composition for optical elements of the present invention, a commonly-known additive such as titanium dioxide, manganese carbonate, $Fe_2O_3$, ferrite, mica, glass fibers, or glass flakes may be added. The amount of such an optional ingredient is desirably as low as possible so as not to inhibit the effects of the present invention.

The composition for optical elements of the present invention may be provided by uniformly mixing the aforementioned ingredients with a kneading apparatus such as a roll mill, a Banbury mixer, or a kneader, or with a planetary stirring and defoaming apparatus and then, if necessary, heating the mixture.

The composition for optical elements of the present invention may be used as a molding material. The composition may be molded by any method, such as extrusion molding, compression molding, blow molding, calender molding, vacuum forming, foam molding, injection molding, liquid injection molding, and cast molding.

A cured product (optical element) from the composition for optical elements of the present invention has excellent heat, light and blue-violet-laser resistances. The cured product also has high light transmittance even to near-ultraviolet rays having a wavelength of about 400 nm.

<Insulator>

The insulator of the present invention may be provided as follows: first, a curing agent and, if necessary, a hydrosilylation catalyst, a curing retardant, an adhesion promoter, and a solvent are added to the modified polyhedral polysiloxane to provide a uniformly mixed composition; next, for example, the composition is applied to a substrate and then heated to remove the solvent; and subsequently, the composition is allowed to cure to provide the insulator.

The solvent is not particularly limited. Specific examples thereof include ethylene dichloride, cyclohexanone, cyclopentanone, 2-heptanone, methylisobutyl ketone, γ-butyrolactone, methylethyl ketone, methanol, ethanol, dimethylimidazolidinone, ethylene glycol monomethyl ether, ethylene glycol monoethyl ether, ethylene glycol dimethyl ether, 2-methoxyethylacetate, ethylene glycolmonoethyl ether acetate, propylene glycol monomethyl ether (PGME), propylene glycol monomethyl ether acetate (PGMEA), tetraethylene glycol dimethyl ether, triethylene glycol monobutyl ether, triethylene glycol monomethyl ether, diethylene glycol dimethyl ether, diethylene glycol diethyl ether, isopropanol, ethylene carbonate, ethyl acetate, butyl acetate, methyl lactate, ethyl lactate, methyl methoxypropionate, ethyl ethoxypropionate, methyl pyruvate, ethyl pyruvate, propyl pyruvate, N,N-dimethyl formamide, dimethyl acetamide, dimethyl sulfoxide, N-methyl pyrolidone, tetrahydrofuran, diisopropyl benzene, toluene, xylene, and mesitylene. Each of these solvents may be used singly, or two or more of these may be used in admixture.

The substrate material is not particularly limited. It may be a substrate with components such as electronic components, optical components, semiconductor elements, and metal wirings mounted thereon. Specific examples thereof include semiconductor integrated circuits comprising solid elements such as liquid crystal display elements, transistors, and diodes, as well as substrate materials such as glasses, glass epoxies, silicon wafers, $SiO_2$ wafers, and SiN wafers.

The method for applying the composition to a substrate is not particularly limited. Examples thereof include conventionally known methods such as spin coating, roll coating, dipping, and spraying. The film thickness may be adjusted depending on the use and is not particularly limited. It is 0.01 to 100 μm, desirably 0.05 to 50 μm, and more desirably 0.1 to 20 μm in a dried state.

The heating method is not particularly limited as long as the temperature can be controlled to a predetermined value. Specifically, for example, an oven, a hot plate, or an infrared oven may be used. Heating may be performed under any atmosphere such as air, nitrogen atmosphere, argon atmosphere, vacuum, or reduced pressure with a controlled oxygen concentration, depending on the use. The heating temperature is also not particularly limited. It is desirably 30° C. to 600° C., and more desirably 50° C. to 500° C. A higher temperature may cause poor appearance of the insulator, and a lower temperature may cause insufficient curing.

Curing may be performed using combinations between two or more temperature conditions. Specifically, the curing temperature is desirably stepwise increased, for example, to 70° C., then to 120° C., and finally to 150° C., because such increase makes it possible to provide a favorable insulator. The heating time period may be set depending on the curing temperature, the amounts of a hydrosilylation catalyst to be used and a hydrosilyl group, and the combination of other ingredients. For example, a favorable insulator may be provided by a curing reaction for 1 minute to 12 hours, and desirably for 10 minutes to 8 hours.

If necessary, the insulator of the present invention may contain a pore-forming agent (foaming agent) for reducing dielectric constant in any amount as long as the film can maintain sufficient mechanical strength. The pore-forming agent is not particularly limited. It desirably has both solubility to a solvent and compatibility with the composition.

Examples of a polymer used as the pore-forming agent include: polyvinyl aromatic compounds such as polystyrene, polyvinyl pyridine, and halogenated polyvinyl aromatic compounds; polyacrylonitrile; polyalkylene oxides such as polyethylene oxide and polypropylene oxide; polyethylene; polylactic acid; polysiloxane; polycaprolactone; polycaprolactum; polyurethane; polymethacrylates such as polymethyl methacrylate, and polymethacrylic acid; polyacrylates such as polymethyl acrylate, and polyacrylic acid; polydienes such as polybutadiene and polyisoprene; polyvinyl chloride; polyacetal; and amine-capped alkylene oxide.

Examples thereof further include polyphenylene oxide, poly(dimethylsiloxane), polytetrahydrofuran, polycyclohexylethylene, polyethyloxazoline, polyvinyl pyridine, and polycaprolactone.

In particular, polystyrene is suitably used as the pore-forming agent. Examples of the polystyrene include anionically polymerized polystyrene, syndiotactic polystyrene, and unsubstituted or substituted polystyrenes such as poly(α-methylstyrene). Desirable among these are unsubstituted polystyrenes.

The insulator of the present invention has high transparency as well as low dielectric constant, and thereby it is suitably used from the viewpoint of light extraction efficiency. The insulator of the present invention also has excellent heat and light resistances, so that it allows optical devices to be used for a long time.

The insulator of the present invention can be used in various applications. Specific examples thereof include, but are not limited to: insulators in semiconductor devices such as LSI, system LSI, DRAM, SDRAM, RDRAM, D-RDRAM, and TFT, and in electronic components such as multi-chip module multilayer circuit boards; interlayer insulators for semiconductors; etching stopper films; surface protective films; buffer coating films; passivation films; α-ray blocking films; coverlay films for flexographic printing plates; overcoat films; cover coatings for flexible copper laminate; solder-resist films; liquid crystal alignment films; and planarizing films.

EXAMPLES

The composition of the present invention will be described below in more detail by reference to Examples. However, the invention should not be construed as being limited to these Examples.

(Heat Resistance Test)

In a hot air circulation oven whose temperature was adjusted to 200° C., a 3 mm-thick plate-shaped molded product was aged for 24 hours, and then the light transmittance after aging was measured, or, the change of appearance was evaluated as follows; the molded product was evaluated as "good" in the case where no change of the appearance was observed, while the molded product was evaluated as "poor" in the case where coloring was observed thereon.

(Light Resistance Test)

Metaling Weather Meter (Type "M6T") produced by Suga Test Instruments Co., Ltd. was used. At a black panel temperature of 120° C. and an irradiance of 0.53 kW/m$^2$, a sample was irradiated to have an integrated irradiance of 50 MJ/m$^2$. Thereafter, the light transmittance was measured, or, the change of appearance was evaluated as follows; the sample was evaluated as "good" in the case where no change of the appearance was observed, while the sample was evaluated as "poor" in the case where coloring was observed thereon.

(Light Transmittance)

The light transmittance at a wavelength of 700 nm and/or 400 nm was measured at a temperature of 20° C. and at a humidity of 50% by using an ultraviolet and visible spectrophotometer V-560 (produced by Jasco Corporation).
(Blue-Violet-Laser Resistance Test)

A sample was irradiated with blue-violet-laser light having a wavelength of 400 to 415 nm and an irradiance of 100 W/mm², at a temperature of 60° C. for 2 hours, by using a laser diode (produced by Nichia Corporation, product name: NDHV310APC). At this time, the laser transmittance at the time of the initiation and the end of laser radiation was measured with a power meter (produced by Coherent Japan, Inc., product name: LM-2VIS), and the laser transmittance change was calculated by the following calculating formula.

[Laser transmittance change]=[(Laser transmittance at the initiation of the test)−(Laser transmittance at the end of the test)]×100/(Laser transmittance at the initiation of the test)

At the same time, the sample after the laser radiation was visually observed for the presence of appearance change in the laser irradiated part; and the sample was evaluated as "good" in the case where no change was observed, while the sample was evaluated as "poor" in the case where stripes and/or surface irregularities were clearly formed in the irradiated part. The sample evaluated as "good" was further observed with an optical microscope, and the sample was downgraded to "acceptable" when slight surface irregularities and/or slight stripes were found in the irradiated part.
(Adhesion Test)

A polysiloxane composition (150 g/m²) was applied to one side of a glass chip (2 mm square), laminated on a glass epoxy board (produced by Taiyu Kizai Co., Ltd.), and heated at 60° C. for 3 hours, at 80° C. for 1 hour, at 100° C. for 1 hour, at 120° C. for 1 hour, at 150° C. for 1 hour, and at 180° C. for 1 hour. After the laminate was cooled down to room temperature, the adhesive strength between the glass chip and the glass epoxy board was measured using a bond tester SERIES4000 (produced by Dage). In this test, the adhesive strength is desirably 0.3 Kgf or higher, more desirably 1.0 Kgf or higher, and further more desirably 1.5 Kgf or higher.
(Thermal Dimensional Stability Test)

A thermomechanical analyzer TMA-50 (produced by Shimadzu Corporation) was used. The coefficient of thermal expansion (CTE, unit: ppm) of a sample was measured under nitrogen atmosphere from 40° C. to 250° C. at a rate of temperature rise of 10° C./min, and the values at 150° C. were used. Table 4 shows the results.
(Hardness Measuring Test)

An ASKER hardness tester Type D (produced by Kobunshi Keiki Co., Ltd.) was used.

When a numerical value of the test result is large, the hardness is high, and thereby surface scratch resistance, etc. are excellent.

Example 1

At 70° C. for 3 hours, a mixed solution containing 2.0 g of octa (dimethylsiloxy) octasilsesquioxane (produced by Mayaterials, Inc.) as a dimethylsiloxy group-containing polyhedral polysiloxane compound, 4.0 g of toluene, 1.75 g of vinyltrimethoxysilane, and 1.18 µL of a platinum-vinylsiloxane complex (Pt-VTSC-3.0x, produced by NEM Cat) was reacted. Toluene was distilled off after the reaction to provide 3.7 g of a modified polyhedral polysiloxane (intermediate) that had six alkoxysilyl groups and two dimethylsiloxy groups on average.

Then, 50 g of methanol and 1.8 g of water were added to 2.5 g of the modified polyhedral polysiloxane (intermediate). The resultant mixture was stirred at room temperature for 6 hours, and the solvents were distilled off to give the target silanol group-containing modified polyhedral polysiloxane (compound I). It was visually observed that the compound I was dissolved in a 25% tetramethylammonium hydroxide aqueous solution.

Example 2

To 1 g of the compound I obtained in Example 1 was added 0.005 g of RHODORSIL-PI2074 (onium salt as a photocuring initiator, produced by Rhodia), and then stirred for mixing. The composition thus obtained was applied to a 0.7 mm-thick glass substrate. About half of the glass substrate dimension was covered with a 3-mm-thick black plastic board, and the glass substrate was irradiated for 50 seconds by using a radiation delivery apparatus (produced by Eye Graphics Co., Ltd., irradiation distance: 80 mm, with a 3000-W metal halide lamp). The sample obtained was immersed in a 25% tetramethylammonium hydroxide aqueous solution for 1 minute, and thereafter sufficiently washed with water.

The sample thus obtained was observed. The part of the sample covered with the black plastic board at the time of radiation irradiation had no resin attached thereto, and thus the composition applied thereto was dissolved in the alkaline aqueous solution. On the other hand, the composition applied to the part not covered with the black plastic board was not dissolved in the alkaline aqueous solution, and the polysiloxane film was laminated in the part.

In a hot air circulation oven whose temperature was adjusted to 200° C., the glass substrate coated with the polysiloxane film was aged at 200° C. for 24 hours. The appearance of the obtained sample was then observed, and no change of the film transparency was (visually) observed.

The glass substrate coated with the polysiloxane film was further observed with a metaling weather meter (produced by Suga Test Instruments Co., Ltd., Type "M6T"). At a black panel temperature of 120° C. and an irradiance of 0.53 kW/m², the glass substrate was irradiated to have an integrated irradiance of 50 MJ/m². The appearance of the obtained sample was observed, and no change of the film transparency was (visually) observed.

Production Example 1

Tetraalkoxysilane (1354 g) was added to 1674 g of a 48% choline aqueous solution, and vigorously stirred at room temperature for 2 hours. Stirring was slowed down when heat was generated in the reaction system to give a homogeneous solution; and then the solution was further reacted for 12 hours. Subsequently, methanol (1400 mL) was added to a solid (hereinafter, also referred to as the compound II) generated in the reaction system to give a homogeneous solution.

The methanol solution of the compound II was slowly added dropwise to a solution of 1569 g of dimethylvinylchlorosilane and 1000 mL of hexane under vigorous stirring. After the dropwise addition, the resultant mixture was reacted for 1 hour. Thereafter, an organic layer was extracted therefrom and condensed to give a solid. Subsequently, the generated solid was vigorously stirred in methanol to be washed, and filtered, so that 740 g of octa(vinyldimethylsiloxy)octasilsesquioxane was obtained as a white solid.

Production Example 2

After a mixed solution containing 34.5 g of a 48% choline aqueous solution and 27.9 g of tetraethoxysilane was stirred at room temperature for 4 hours, 30 mL of methanol was added to the mixed solution to give a homogeneous solution. Subsequently, the prepared homogeneous solution was added dropwise to a stirred solution of 16.15 g of dimethylchlorovinylsilane, 14.53 g of trimethylchlorosilane, and hexane (50 mL). After the dropwise addition, the resultant mixture was stirred for 3 hours at room temperature. Then, hexane was added thereto, and an organic layer was extracted and condensed under reduced pressure. The obtained crude product was washed with methanol and suction-filtered to give 10 g of octasilsesquioxane containing a vinyldimethylsiloxy group and a trimethylsiloxy group whose average composition is represented by the following formula:

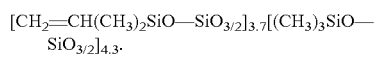

[CH$_2$=CH(CH$_3$)$_2$SiO—SiO$_{3/2}$]$_{3.7}$[(CH$_3$)$_3$SiO—SiO$_{3/2}$]$_{4.3}$.

Example 3

5.0 g of octa(vinyldimethylsiloxy)octasilsesquioxane (a polyhedral polysiloxane compound) was dissolved in 2.0 g of toluene and 8.76 g of tetramethyldisiloxane. Thereafter, 0.49 µL of a xylene solution of a platinum-vinylsiloxane complex (the amount of platinum in the platinum-vinylsiloxane complex: 3 wt %, produced by Umicore Japan K.K., Pt-VTSC-3X) was added to the resultant solution, and reacted at 80° C. for 3 hours. After the reaction, toluene and an excess amount of tetramethyldisiloxane were distilled off to give 8.57 g of a modified polyhedral polysiloxane (hereinafter, also referred to as the compound III). The obtained modified polyhedral polysiloxane was a transparent liquid, and it was verified by $^1$H-NMR that a SiH group derived from tetramethyldisiloxane was introduced therein.

Example 4

1.0 g of octa(vinyldimethylsiloxy)octasilsesquioxane (a polyhedral polysiloxane compound) was dissolved in 1.0 g of toluene and 5.87 g of a linear polydimethylsiloxane containing hydrosilyl groups at the both ends (DMS-H03, produced by Gelest Inc.). Thereafter, 0.1 µL of a xylene solution of a platinum-vinylsiloxane complex (the amount of platinum in the platinum-vinylsiloxane complex: 3 wt %, produced by Umicore Japan K.K., Pt-VTSC-3X) was added to the resultant solution, and reacted at 80° C. for 3 hours. After the reaction, toluene was distilled off to give 6.37 g of a polysiloxane compound. The obtained compound was a transparent liquid, and it was verified by $^1$H-NMR that a SiH group derived from the linear polydimethylsiloxane containing hydrosilyl groups at the both ends was introduced therein.

Example 5

3.0 g of octa(vinyldimethylsiloxy)octasilsesquioxane (a polyhedral polysiloxane compound) was dissolved in 3.0 g of toluene and 11.77 g of 1,3,5,7-tetrahydrogen-1,3,5,7-tetramethylcyclotetrasiloxane. Thereafter, 2.2 µL of a xylene solution of a platinum-vinylsiloxane complex (the amount of platinum in the platinum-vinylsiloxane complex: 3 wt %, produced by Umicore Japan K.K., Pt-VTSC-3X) was added to the resultant solution, and reacted at 80° C. for 3 hours.

After the reaction, toluene and an excess amount of 1,3,5,7-tetrahydrogen-1,3,5,7-tetramethylcyclotetrasiloxane were distilled off to give 6.53 g of a modified polysiloxane (hereinafter, also referred to as the compound IV). The obtained modified polysiloxane was a transparent liquid, and it was verified by $^1$H-NMR that a SiH group derived from 1,3,5,7-tetrahydrogen-1,3,5,7-tetramethylcyclotetrasiloxane was introduced therein.

Example 6

10 g of octa(vinyldimethylsiloxy)octasilsesquioxane obtained in Production Example 1 and 2.4 µL of a xylene solution of a platinum-vinylsiloxane complex (the amount of platinum in the platinum-vinylsiloxane complex: 3 wt %, produced by Umicore Japan K.K., Pt-VTSC-3X) were dissolved in 15 g of methylcyclohexane. Then, the solution thus obtained was slowly added dropwise to a solution in which 40 g of 1,3,5,-tetrahydrogen-1,3,5,7-tetramethylcyclotetrasiloxane was dissolved in 40 g of methylcyclohexane, and the obtained mixture was reacted at 95° C. for 3 hours.

After the reaction, methylcyclohexane and an excess amount of 1,3,5,7-tetrahydrogen-1,3,5,7-tetramethylcyclotetrasiloxane were distilled off to give 23 g of a modified polysiloxane. The obtained modified polysiloxane was a colorless, transparent liquid, and it was verified by $^1$H-NMR that a SIR group derived from 1,3,5,7-tetrahydrogen-1,3,5,7-tetramethylcyclotetrasiloxane was introduced therein.

Example 7

A mixed solution of 0.96 g of the polyhedral polysiloxane compound obtained in Production Example 2, 0.30 µL of a platinum-vinylsiloxane complex (the amount of platinum in the platinum-vinylsiloxane complex: 3 wt %, produced by Umicore Japan K.K., Pt-VTSC-3X), and 4 g of methylcyclohexane was added dropwise to a mixed solution of 1.82 g of 1,3,5,7-tetrahydrogen-1,3,5,7-tetramethylcyclotetrasiloxane and 2 g of methylcyclohexane. Then, the mixture was heated at 95° C. for 6.5 hours, and then cooled down to room temperature.

After the reaction, methylcyclohexane and an excess amount of 1,3,5,7-tetrahydrogen-1,3,5,7-tetramethylcyclotetrasiloxane were distilled off to give 1.47 g of a modified polysiloxane. The obtained modified compound was a colorless, transparent liquid, and it was verified by $^1$H-NMR that a SiH group derived from 1,3,5,7-tetrahydrogen-1,3,5,7-tetramethylcyclotetrasiloxane was introduced therein.

Example 7-1

2.0 g of octa(vinyldimethylsiloxy)octasilsesquioxane (a polyhedral polysiloxane compound) was dissolved in 2.0 g of toluene and 1.57 g of 1,3,5,7-tetrahydrogen-1,3,5,7-tetramethylcyclotetrasiloxane. Thereafter, 0.1 µL of a xylene solution of a platinum-vinylsiloxane complex (the amount of platinum in the platinum-vinylsiloxane complex: 3 wt %, produced by Umicore Japan K.K., Pt-VTSC-3X) was added to the resultant solution, and reacted at 80° C. for 3 hours. After the reaction, a gelatinous polysiloxane compound was formed.

Example 8

0.21 g of 1,3,5,7-tetravinyl-1,3,5,7-tetramethylcyclotetrasiloxane was added to 1.0 g of the compound III (the liquid modified product) to give a polysiloxane composition as a homogeneous liquid. The composition thus obtained was poured into a mold, and cured by heating at 70° C. for 30 minutes, at 120° C. for 10 minutes, and at 150° C. for 10 minutes to give a 3 mm-thick molded product for evaluation. The molded product thus obtained was evaluated for the initial light transmittance, the light transmittance after a heat resistance test, and the light transmittance after a light resistance test. Table 1 shows the results.

Example 9

0.77 g of a linear polydimethylsiloxane containing vinyl groups at the both ends (produced by Clariant Japan K.K., trade name: MVD8MV) was added to 1.0 g of the compound III to give a polysiloxane composition as a homogeneous liquid. The composition thus obtained was poured into a mold, and cured by heating at 70° C. for 30 minutes, at 120° C. for 10 minutes, and at 150° C. for 10 minutes to give a 3 mm-thick molded product for evaluation. The molded product thus obtained was evaluated for the initial light transmittance, the light transmittance after a heat resistance test, and the light transmittance after a light resistance test. Table 1 shows the results.

Example 10

0.70 g of MQ resin containing a vinyl group at the end (produced by Clariant Japan K.K., trade name: MQV-7) was added to 1.0 g of the compound III to give a polysiloxane composition as a homogeneous solution. The composition thus obtained was poured into a mold, and cured by heating at 70° C. for 30 minutes, at 120° C. for 10 minutes, and at 150° C. for 10 minutes to give a 3 mm-thick molded product for evaluation. The molded product thus obtained was evaluated for the initial light transmittance, the light transmittance after a heat resistance test, and the light transmittance after a light resistance test. Table 1 shows the results.

Example 11

0.62 g of 1,3,5,7-tetravinyl-1,3,5,7-tetramethylcyclotetrasiloxane was added to 1.5 g of the compound IV to give a polysiloxane composition as a homogeneous solution. The composition thus obtained was poured into a mold, and cured by heating at 70° C. for 30 minutes, at 120° C. for 10 minutes, and at 150° C. for 10 minutes to give a 3 mm-thick molded product for evaluation. The molded product thus obtained was evaluated for the initial light transmittance, the light transmittance after a heat resistance test, and the light transmittance after a light resistance test. Table 1 shows the results.

Example 12

2.27 g of a linear polydimethylsiloxane containing vinyl groups at the both ends (produced by Clariant Japan K.K., trade name: MVD8V) was added to 1.5 g of the compound IV to give a polysiloxane composition as a homogeneous liquid. The composition thus obtained was poured into a mold, and cured by heating at 70° C. for 30 minutes, at 120° C. for 10 minutes, and at 150° C. for 10 minutes to give a 3 mm-thick molded product for evaluation. The molded product thus obtained was evaluated for the initial light transmittance, the light transmittance after a heat resistance test, and the light transmittance after a light resistance test. Table 1 shows the results.

Example 13

2.06 g of MQ resin containing a vinyl group at the end (produced by Clariant Japan K.K., trade name: MQV-7) was added to 1.5 g of the compound IV to give a polyhedral polysiloxane composition as a homogeneous solution. The composition thus obtained was poured into a mold, and cured by heating at 70° C. for 30 minutes, at 120° C. for 10 minutes, and at 150° C. for 10 minutes to give a 3 mm-thick molded product for evaluation. The molded product thus obtained was evaluated for the initial light transmittance, the light transmittance after a heat resistance test, and the light transmittance after a light resistance test. Table 1 shows the results.

Example 14

3.0 g of a polysiloxane containing a vinyl group at the end (MQV7, produced by Clariant Japan K.K.) was added to 3.5 g of the modified polyhedral polysiloxane obtained in Example 7 to prepare a polysiloxane composition. The polysiloxane composition thus obtained was poured into a mold, and cured by heating at 60° C. for 3 hours, at 80° C. for 1 hour, at 100° C. for 1 hour, at 120° C. for 1 hour, at 150° C. for 1 hour, and at 180° C. for 1 hour to give a 3 mm-thick molded product for evaluation. The molded product thus obtained was evaluated for the initial light transmittance, the light transmittance after a heat resistance test, and the light transmittance after a light resistance test. Table 1 shows the results.

Example 15

2.5 g of a linear polydimethylsiloxane containing vinyl groups at the both ends (produced by Clariant Japan K.K., trade name: MVD8MV) was added to 1.5 g of the modified polyhedral polysiloxane obtained in Example 6 to produce a polysiloxane composition. The polysiloxane composition thus obtained was poured into a mold, and cured by heating at 60° C. for 1 hour, at 80° C. for 1 hour, at 100° C. for 1 hour, at 120° C. for 1 hour, at 150° C. for 1 hour, and at 180° C. for 1 hour to give a 3 mm-thick cured product for evaluation. The molded product thus obtained was evaluated for light transmittance, and the cured product was subjected to a heat resistance test, a light resistance test, and a blue-violet-laser resistance test. Table 1 shows the results.

Example 16

4.1 g of a linear polydimethylsiloxane containing a vinyl group at the end (MVD8MV, produced by Clariant Japan K.K.) was added to 3.5 g of the modified polyhedral polysiloxane obtained in Example 7 to produce a polysiloxane composition. The polysiloxane composition thus obtained was poured into a mold, and cured by heating at 60° C. for 3 hours, at 80° C. for 1 hour, at 100° C. for 1 hour, at 120° C. for 1 hour, at 150° C. for 1 hour, and at 180° C. for 1 hour to give a 3 mm-thick molded product for evaluation. The molded product thus obtained was evaluated for the initial light transmittance, the light transmittance after a heat resistance test, and the light transmittance after a light resistance test. Further, the molded product was subjected to a blue-violet-laser resistance test. Table 1 shows the results.

TABLE 1

| | Light transmittance (%) | | | | | | Blue-violet-laser resistance | |
| --- | --- | --- | --- | --- | --- | --- | --- | --- |
| | Initial value | | After light resistance test | | After heat resistance test | | Change of transmittance | Change of |
| | 700 nm | 400 nm | 700 nm | 400 nm | 700 nm | 400 nm | (%) | appearance |
| Example 8 | 90 | 89 | 89 | 88 | 87 | 85 | | |
| Example 9 | 79 | 78 | 87 | 85 | 82 | 79 | | |
| Example 10 | 95 | 95 | 94 | 94 | 93 | 92 | | |
| Example 11 | 94 | 93 | 93 | 91 | 95 | 93 | | |
| Example 12 | 93 | 91 | 91 | 89 | 92 | 90 | | |
| Example 13 | 92 | 90 | 90 | 88 | 92 | 90 | | |
| Example 14 | 93 | 91 | 93 | 91 | 92 | 90 | | |
| Example 15 | 93 | 91 | 94 | 91 | 93 | 91 | 0 | Good |
| Example 16 | 93 | 90 | 92 | 90 | 92 | 90 | 0 | Good |
| Example 20 | 93 | 92 | 92 | 88 | 92 | 88 | NA | NA |
| Example 21 | NA | 92 | NA | 92 | NA | 92 | 0 | Good |
| Example 24 | NA | 89 | NA | 90 | NA | 89 | 0 | Good |
| Example 25 | NA | 91 | NA | 92 | NA | 91 | NA | NA |
| Example 34 | NA | 90 | NA | 90 | NA | 90 | 0 | Good |
| Comparative Example 1 | NA | 89 | NA | 49 | NA | 87 | NA | NA |

NA = Not Available

Example 17

1.65 g of a linear polydimethylsiloxane containing a vinyl group at the end (MVD8MV, produced by Clariant Japan K.K.) and 0.07 g of 3-glycidoxypropyltrimetoxysilane were added to 1.0 g of the modified polyhedral polysiloxane obtained in Example 6 to produce a polysiloxane composition. The polysiloxane composition thus obtained was poured into a mold, and cured by heating at 60° C. for 3 hours, at 80° C. for 1 hour, at 100° C. for 1 hour, at 120° C. for 1 hour, at 150° C. for 1 hour, and at 180° C. for 1 hour to give a 3 mm-thick molded product for evaluation. The molded product thus obtained was subjected to a heat resistance test and a light resistance test. Also, the obtained composition was subjected to an adhesion test. Table 2 shows the results.

Example 18

1.65 g of a linear polydimethylsiloxane containing a vinyl group at the end (MVD8MV, produced by Clariant Japan K.K.) was added to 1.0 g of the modified polyhedral polysiloxane obtained in Example 6 to produce a polysiloxane composition. The polysiloxane composition thus obtained was poured into a mold, and cured by heating at 60° C. for 3 hours, at 80° C. for 1 hour, at 100° C. for 1 hour, at 120° C. for 1 hour, at 150° C. for 1 hour, and at 180° C. for 1 hour to give a 3 mm-thick molded product for evaluation. The molded product thus obtained was subjected to a heat resistance test and a light resistance test. Also, the obtained composition was subjected to an adhesion test. Table 2 shows the results.

TABLE 2

| | Adhesion test (kgf) | After heat resistance test | After light resistance test |
| --- | --- | --- | --- |
| Example 17 | 2 | Good | Good |
| Example 18 | 0.6 | Good | Good |

Example 19

A mixed solution of 3.0 g of octavinyloctasilsesquioxane (produced by Hybrid Plastics Inc.), 4.3 μL of a platinum-vinylsiloxane complex (3% platinum, in xylene solution), and 3.0 mL of toluene was added dropwise to a mixed solution of 23 g of 1,3,5,7-tetrahydrogen-1,3,5,7-tetramethylcyclotetrasiloxane and 23 mL of toluene. Then, the resultant mixture was heated at 80° C. for 3.5 hours, and then cooled down to room temperature. Toluene and an unreacted portion of the 1,3,5,7-tetrahydrogen-1,3,5,7-tetramethylcyclotetrasiloxane in the obtained reaction solution were distilled off to give 10.68 g of a modified polyhedral polysiloxane.

Example 20

6.0 g of a linear polydimethylsiloxane containing a vinyl group at the end (MVD8MV, produced by Clariant Japan K.K.) was added to 3.0 g of the modified polyhedral polysiloxane obtained in Example 19 to prepare a polysiloxane composition. The polysiloxane composition thus obtained was poured into a mold, and cured by heating at 60° C. for 3 hours, at 80° C. for 1 hour, at 100° C. for 1 hour, at 120° C. for 1 hour, at 150° C. for 1 hour, and at 180° C. for 1 hour to give a 3 mm-thick molded product for evaluation. The molded product for evaluation thus obtained was subjected to a heat resistance test and a light resistance test, and was evaluated for the light transmittances before and after these tests. Table 1 shows the results.

Production Example 3

3.0 g of octa(vinyldimethylsiloxy)octasilsesquioxane (a polyhedral polysiloxane compound) and 0.7 μL of a xylene solution of a platinum-vinylsiloxane complex (produced by Umicore Japan K.K., Pt-VTSC-3X) were dissolved in 3.0 g of methylcyclohexane. Then, the solution thus obtained was slowly added dropwise to a solution in which 12 g of 1,3,5, 7-tetrahydrogen-1,3,5,7-tetramethylcyclotetrasiloxane was dissolved in 12 g of methylcyclohexane, and the obtained mixture was reacted at 95° C. for 3 hours. The resultant reaction mixture was cooled down to room temperature, and 0.3 μL of dimethyl malate was added thereto.

After the reaction, methylcyclohexane and an excess amount of 1,3,5,7-tetrahydrogen-1,3,5,7-tetramethylcyclotetrasiloxane were distilled off to give 6.53 g of a modified polyhedral polysiloxane (hereinafter, also referred to as the compound V). The obtained compound was a transparent liquid, and it was verified by $^1$H-NMR that a SiH group derived from 1,3,5,7-tetrahydrogen-1,3,5,7-tetramethylcyclotetrasiloxane was introduced therein.

Example 21

2.4 g of a linear polydimethylsiloxane containing vinyl groups at the both ends (produced by Clariant Japan K.K., trade name: MVD8MV) and 0.1 µL of a xylene solution of a platinum-vinylsiloxane complex (produced by Umicore Japan K.K., Pt-VTSC-3X) were added to 1.5 g of the compound V obtained in Production Example 3 to give a homogeneous composition, so that an encapsulant for optical elements was obtained.

The encapsulant for optical elements thus obtained was poured into a mold, and cured by heating at 60° C. for 1 hour, at 80° C. for 1 hour, at 100° C. for 1 hour, at 120° C. for 1 hour, at 150° C. for 1 hour, and at 180° C. for 1 hour to give a 3 mm-thick cured product for evaluation. The molded product thus obtained was evaluated for light transmittance, and the cured product was subjected to a heat resistance test, a light resistance test, and a blue-violet-laser resistance test. Table 1 shows the results.

Example 22

One dummy silicon chip as an optical element (size: 0.4 mm×0.4 mm×0.2 mm) was fixed to the inside bottom of a package (TOPLED1-IN-1, produced by Enomoto Co., Ltd.) with an epoxy adhesive to produce a package for evaluation of the ability to seal an optical element. 0.05 g of SH6040 (produced by Dow Corning Toray Co., Ltd.) was added as an adhesion promoter to the encapsulant for optical elements obtained in Example 21 to give a homogeneous composition, so that another encapsulant for optical elements was obtained.

The encapsulant for optical elements thus obtained was poured into the package for evaluation of the ability to seal an optical element by using an air dispenser, and cured by heating at 60° C. for 1 hour, at 80° C. for 1 hour, at 100° C. for 1 hour, at 120° C. for 1 hour, and at 150° C. for 1 hour and then checked for sealing of the chip.

Example 23

Three dummy silicon chips as optical elements (size: 5 mm×5 mm×0.2 mm) were fixed to a glass epoxy substrate (100 mm×50 mm×0.3 mm) with an epoxy adhesive to produce a package for evaluation of the ability to seal optical elements.

The encapsulant for optical elements obtained in Example 22 was applied to the substrate for evaluation, and cured by heating at 60° C. for 1 hour, at 80° C. for 1 hour, at 100° C. for 1 hour, at 120° C. for 1 hour, and at 150° C. for 1 hour and then checked for sealing of the chips. It was verified that it was possible to favorably dice (singulate) the obtained sealed optical element substrate with a diamond cutter.

As thus described, the encapsulant for optical elements of the present invention can be treated as a transparent liquid composition, and is excellent in handleability, light transmittance (transparency), and heat, light, and blue-violet-laser resistances. Since the encapsulant for optical elements excels in adhesion to a substrate, a chip can be favorably sealed therewith. It is possible to perform singulation after sealing the substrate therewith, leading to excellent processability.

Example 24

2.3 g of a linear polydimethylsiloxane containing vinyl groups at the both ends (produced by Clariant Japan K.K., trade name: MVD8MV), 0.3 g of a linear polydimethylsiloxane (produced by Gelest Inc., trade name: DMS-V31), and 0.1 µL of a xylene solution of a platinum-vinylsiloxane complex (produced by Umicore Japan K.K., Pt-VTSC-3X) were added to 1.5 g of the compound V obtained in Production Example 3 to give a composition for optical elements. The composition thus obtained was poured into a mold, and cured by heating at 60° C. for 1 hour, at 80° C. for 1 hour, at 100° C. for 1 hour, at 120° C. for 1 hour, at 150° C. for 1 hour, and at 180° C. for 1 hour to give a 3 mm-thick molded product for an optical element. The molded product thus obtained was evaluated for light transmittance, and the molded product was subjected to a heat resistance test, a light resistance test, and a blue-violet-laser resistance test. Table 1 shows the results.

Example 25

The composition for optical elements obtained in Example 24 was applied to a glass substrate (100 mm×50 mm×0.7 mm), and cured by heating at 60° C. for 3 hours, at 80° C. for 2 hours, at 100° C. for 1 hour, at 120° C. for 1 hour, at 150° C. for 1 hour, and at 180° C. for 1 hour. The material for an optical element thus obtained was evaluated for light transmittance, and subjected to a heat resistance test and a light resistance test. Table 1 shows the results.

Comparative Example 1

A composition comprising 0.2 g of a curing catalyst and 10 g of an epoxy resin (Celloxide 2021P, produced by Daicel Chemical Industries, Ltd.) was applied to a glass substrate (100 mm×50 mm×0.7 mm), and cured by heating at 90° C. for 1 hour and at 120° C. for 1 hour. The material for an optical element thus obtained was evaluated for light transmittance, and subjected to a heat resistance test and a light resistance test. Table 1 shows the results.

Example 26

The composition for optical elements obtained in Example 24 was applied to a glass substrate (100 mm×50 mm×0.7 mm), and a silicon mold having 5-µm-width lines & spaces was pressed thereto with a load of 0.5 kg applied thereto. The composition was cured by heating at 60° C. for 3 hours, at 80° C. for 2 hours, at 100° C. for 1 hour, at 120° C. for 1 hour, at 150° C. for 1 hour, and at 180° C. for 1 hour. The sample was released from the mold, whereby a material for an optical element in which a fine groove structure was transferred on the glass plate was obtained.

Example 27

The composition for optical elements obtained in Example 24 was applied to a glass substrate (100 mm×50 mm×0.7 mm), and a silicon mold having a 1-µm-size hole structure was pressed thereto with a load of 0.5 kg applied thereto. The composition was cured by heating at 60° C. for 3 hours, at 80° C. for 2 hours, at 100° C. for 1 hour, at 120° C. for 1 hour, at 150° C. for 1 hour, and at 180° C. for 1 hour. The sample was released from the mold, whereby a material for an optical element having a fine dot structure on the glass plate was obtained.

As thus described, the composition for optical elements of the present invention can be treated as a transparent liquid composition, and is excellent in handleability, light transmittance (transparency), and heat, light, and blue-violet-laser resistances. The composition can be also used as a coating material of substrates such as glasses, and it is possible to produce an optical element without impairing heat, light, and blue-violet-laser resistances of the substrates.

Production of Insulator

Example 28

2.4 g of a linear polydimethylsiloxane containing vinyl groups at the both ends (produced by Clariant Japan K.K., trade name: MVD8MV), 0.1 μL of a xylene solution of a platinum-vinylsiloxane complex (produced by Umicore Japan K.K., Pt-VTSC-3X), and 7.8 g of methyl isobutyl ketone were added to 1.5 g of the compound V obtained in Production Example 3 to give a homogeneous solution. The solution thus obtained was applied to a glass substrate (50 mm×100 mm×0.7 mm) by spin coating (1000 rpm, 20 seconds), and cured by heating at 60° C. for 1 hour, at 80° C. for 1 hour, at 100° C. for 1 hour, at 120° C. for 1 hour, at 150° C. for 1 hour, and at 180° C. for 1 hour and then it was verified that a layered body was formed on the glass substrate. The film had a thickness of 2 μm and a favorable adhesion to the substrate.

Production of Molded Product for Evaluation

Example 29

2.4 g of a linear polydimethylsiloxane containing vinyl groups at the both ends (produced by Clariant Japan K.K., trade name: MVD8MV) and 0.1 μL of a xylene solution of a platinum-vinylsiloxane complex (produced by Umicore Japan K.K., Pt-VTSC-3X) were added to 1.5 g of the compound V obtained in Production Example 3 to give a homogeneous solution. The solution thus obtained was poured into a mold, and cured by heating at 60° C. for 1 hour, at 80° C. for 1 hour, at 100° C. for 1 hour, at 120° C. for 1 hour, at 150° C. for 1 hour, and at 180° C. for 1 hour to give a 3 mm-thick molded product for evaluation. The molded product thus obtained was evaluated for light transmittance, and the cured product was subjected to a heat resistance test, a light resistance test, and a dielectric constant test. Table 3 shows the results.

TABLE 3

| | Light transmittance (%) | | | |
|---|---|---|---|---|
| | Initial value | After heat resistance test | After light resistance test | Dielectric constant |
| Example 29 | 92 | 92 | 92 | 2.8 |

As thus described, the insulator of the present invention exhibits a low dielectric constant, and is excellent in handleability, processability, adhesiveness to a substrate, light transmittance (transparency), and heat and light resistances.

Production Example 4

A mixed solution of 10.0 g of octa(vinyldimethylsiloxy) octasilsesquioxane (a polyhedral polysiloxane compound), 15.0 g of methylcyclohexane, and 2.44 μL of a xylene solution of a platinum-vinylsiloxane complex (the amount of platinum in the platinum-vinylsiloxane complex: 3 wt %, produced by Umicore Japan K.K., Pt-VTSC-3X) was slowly added dropwise to a solution of 39.23 g of 1,3,5,7-tetrahydrogen-1,3,5,7-tetramethylcyclotetrasiloxane and 39.23 g of methylcyclohexane under stirring at 80° C. After the dropwise addition, the obtained mixture was further reacted at 80° C. for 5 hours.

After the reaction, methylcyclohexane and an excess amount of 1,3,5,7-tetrahydrogen-1,3,5,7-tetramethylcyclotetrasiloxane were distilled off to give 22.0 g of a modified polyhedral polysiloxane (hereinafter, also referred to as the compound VI).

Example 30

3.30 g of a linear polydimethylsiloxane containing vinyl groups at the both ends (produced by Clariant Japan K.K., trade name: MVDBV) and 2.65 g of fused silica (produced by Tatsumori Ltd., trade name: Fuselex RD-8) were added to 2.0 g of the compound VI obtained in Production Example 4, and sufficiently mixed to give a polysiloxane composition. The composition thus obtained was poured into a mold, and cured by heating at 70° C. for 30 minutes, at 120° C. for 10 minutes, and at 150° C. for 20 minutes to give a 3 mm-thick molded product for evaluation. The molded product thus obtained was evaluated for thermal dimensional stability, hardness, and heat and light resistances. Table 4 shows the results.

Example 31

3.30 g of a linear polydimethylsiloxane containing vinyl groups at the both ends (produced by Clariant Japan K.K., trade name: MVD8V) and 5.30 g of fused silica (produced by Tatsumori Ltd., trade name: Fuselex RD-8) were added to 2.0 g of the compound VI obtained in Production Example 4, and sufficiently mixed to give a polysiloxane composition. The composition thus obtained was poured into a mold, and cured by heating at 70° C. for 30 minutes, at 120° C. for 10 minutes, and at 150° C. for 10 minutes to give a 3 mm-thick molded product for evaluation.

Example 32

3.30 g of a linear polydimethylsiloxane containing vinyl groups at the both ends (produced by Clariant Japan K.K., trade name: MVD8V) and 2.65 g of silica (produced by Nippon Chemical Industrial Co., Ltd., trade name: Silstar LE05S) were added to 2.0 g of the compound VI obtained in Production Example 4, and sufficiently mixed to give a polysiloxane composition. The composition thus obtained was poured into a mold, and cured by heating at 70° C. for 30 minutes, at 120° C. for 10 minutes, and at 150° C. for 10 minutes to give a 3 mm-thick molded product for evaluation.

Example 33

3.30 g of a linear polydimethylsiloxane containing vinyl groups at the both ends (produced by Clariant Japan K.K., trade name: MVD8V) and 5.30 g of silica (produced by Nippon Chemical Industrial Co., Ltd., trade name: Silstar LE05S) were added to 2.0 g of the compound VI obtained in Production Example 4, and sufficiently mixed to give a polysiloxane composition. The composition thus obtained was poured into a mold, and cured by heating at 70° C. for 30 minutes, at 120° C. for 10 minutes, and at 150° C. for 10 minutes to give a 3 mm-thick molded product for evaluation.

Reference Example 1

3.30 g of a linear polydimethylsiloxane containing vinyl groups at the both ends (produced by Clariant Japan K.K., trade name: MVD8V) was added to 2.0 g of the compound VI obtained in Production Example 4, and sufficiently mixed to give a polysiloxane composition. The composition thus obtained was poured into a mold, and cured by heating at 70° C. for 30 minutes, at 120° C. for 10 minutes, and at 150° C. for 10 minutes to give a 3 mm-thick molded product for evaluation.

TABLE 4

| Examples | CTE | Hardness | Heat resistance test | Light resistance test |
| --- | --- | --- | --- | --- |
| Example 30 | 219 | 36 | Good | Good |
| Example 31 | 202 | 48 | Good | Good |
| Example 32 | 226 | 30 | Good | Good |
| Example 33 | 175 | 40 | Good | Good |
| Reference Example 1 | 265 | 20 | Good | Good |

As thus described, the molded product obtained from the siloxane composition of the present invention that contains an inorganic filler as an ingredient has high heat and light resistances, high hardness, small coefficient of thermal expansion, and excellent thermal dimensional stability.

As described above, the modified polyhedral polysiloxane of the present invention can be a transparent liquid, and is easily handled in a transparent liquid state. The molded product obtained from the composition with the modified polyhedral polysiloxane is excellent in heat and light resistances, and exhibits a small decrease in light transmittance.

Production Example 5

10 g of octa(vinyldimethylsiloxy)octasilsesquioxane (a polyhedral polysiloxane compound) and 2.4 µL of a xylene solution of a platinum-vinylsiloxane complex (produced by Umicore Japan K.K., Pt-VTSC-3X) were dissolved in 10 g of methylcyclohexane. Then, the solution thus obtained was slowly added dropwise to a solution in which 39 g of 1,3,5,7-tetrahydrogen-1,3,5,7-tetramethylcyclotetrasiloxane was dissolved in 39 g of methylcyclohexane, and the obtained mixture was reacted at 95° C. for 3 hours. The resultant reaction mixture was cooled down to room temperature, and 0.3 µL of dimethyl malate was added thereto.

After the reaction, methylcyclohexane and an excess amount of 1,3,5,7-tetrahydrogen-1,3,5,7-tetramethylcyclotetrasiloxane were distilled off to give 23 g of a polysiloxane compound (hereinafter, also referred to as the compound VII). The obtained compound was a transparent liquid, and it was verified by $^1$H-NMR that a SiH group derived from 1,3,5,7-tetrahydrogen-1,3,5,7-tetramethylcyclotetrasiloxane was introduced therein.

Example 34

11.5 g of a linear polydimethylsiloxane containing vinyl groups at the both ends (produced by Clariant Japan K.K., trade name: MVD8MV), 2.3 g of a linear polydimethylsiloxane (produced by Gelest Inc., trade name: DMS-V31), and 0.2 µL of a xylene solution of a platinum-vinylsiloxane complex (produced by Umicore Japan K.K., Pt-VTSC-3X) were added to 7.0 g of the compound VII obtained in Production Example 5 to give a polysiloxane composition. The composition thus obtained was poured into a mold, and cured by heating at 60° C. for 1 hour, at 80° C. for 1 hour, at 100° C. for 1 hour, at 120° C. for 1 hour, at 150° C. for 1 hour, and at 180° C. for 1 hour to give a 1 mm-thick cured product. The cured product thus obtained was evaluated for light transmittance, and the cured product was subjected to a heat resistance test, a light resistance test, and a blue-violet-laser resistance test. Table 1 shows the results.

Example 35

The polysiloxane composition obtained in Example 34 was applied to a glass epoxy substrate (100 mm×50 mm×0.3 mm) to have a thickness of about 0.8 mm, and cured by heating at 60° C. for 3 hours, at 80° C. for 2 hours, at 100° C. for 1 hour, at 120° C. for 1 hour, at 150° C. for 1 hour, and at 180° C. for 1 hour. As a result, the glass epoxy substrate had almost no curvature, also had no crack or peeling, and had favorable appearance.

As thus described, the polysiloxane composition of the present invention can be treated as a transparent liquid composition, and is excellent in handleability, light transmittance (transparency), and heat, light, and blue-violet-laser resistances. When the polysiloxane composition is applied to a substrate, it is possible to prevent poor appearance of the substrate, such as curvature, peeling, and cracks.

Example 36

A mixed solution of 5.0 g of octa(vinyldimethylsiloxy)octasilsesquioxane (a polyhedral polysiloxane compound), 7.3 gL of a xylene solution of a platinum-vinylsiloxane complex (the amount of platinum in the platinum-vinylsiloxane complex: 3 wt %, produced by Umicore Japan K.K., Pt-VTSC-3X), and 5.0 g of toluene was slowly added dropwise to a mixed solution of 19.6 g of 1,3,5,7-tetrahydrogen-1,3,5,7-tetramethylcyclotetrasiloxane and 19 g of toluene, which was heated to 80° C., and the obtained mixture was further heated at 80° C. for 1 hour. Then, the mixture was cooled down to room temperature, and 7.5 µL of ethynylcyclohexanol was added thereto. Thereafter, toluene and an unreacted portion of the 1,3,5,7-tetrahydrogen-1,3,5,7-tetramethylcyclotetrasiloxane were distilled off to give a modified polyhedral polysiloxane.

After the obtained modified polyhedral polysiloxane was further dissolved in 15 g of toluene, 0.3 g of allyl glycidyl ether was added thereto. The mixture was reacted at 80° C. for 2 hours and then cooled down to room temperature. Toluene was distilled off from the resultant solution to give 11.5 g of an epoxy group-containing modified polyhedral polysiloxane.

The obtained modified polyhedral polysiloxane was a transparent liquid, and it was verified by $^1$H-NMR that about 22 SiH groups derived from 1,3,5,7-tetrahydrogen-1,3,5,7-tetramethylcyclotetrasiloxane and about 2 glycidyl groups derived from allyl glycidyl ether were introduced therein. 3.7 µL of dimethyl malate was added as a stabilizer to the obtained liquid.

Example 37

4.0 g of a linear polydimethylsiloxane containing vinyl groups at the both ends (produced by Clariant Japan K.K., trade name: MVD8MV) was added to 2.2 g of the polyhedral polysiloxane compound obtained in Example 36 to give a polyhedral polysiloxane composition as a homogeneous solution. The polysiloxane composition thus obtained was poured into a mold, and cured by heating at 60° C. for 1 hour, at 80° C. for 1 hour, at 100° C. for 1 hour, at 120° C. for 1 hour, at 150° C. for 1 hour, and at 180° C. for 1 hour to give a 3 mm-thick molded product for evaluation. The molded product thus obtained was evaluated for light transmittance. The obtained composition was subjected to an adhesion test. Table 5 shows the results.

Reference Example 2

3.0 g of octa(vinyldimethylsiloxy)octasilsesquioxane (a polyhedral polysiloxane compound) was dissolved in 3.0 g of toluene and 11.77 g of 1,3,5,7-tetrahydrogen-1,3,5,7-tetramethylcyclotetrasiloxane. Thereafter, 2.2 µL of a xylene solution of a platinum-vinylsiloxane complex (the amount of platinum in the platinum-vinylsiloxane complex: 3 wt %, produced by Umicore Japan K.K., Pt-VTSC-3X) was added to the resultant solution, and reacted at 80° C. for 3 hours. After the mixture was cooled down to room temperature, 3.8 µL of ethynylcyclohexanol was added thereto.

After the reaction, toluene and an excess amount of 1,3,5,7-tetrahydrogen-1,3,5,7-tetramethylcyclotetrasiloxane were distilled off to give 6.53 g of a polysiloxane compound (hereinafter, also referred to as the compound VIII). The obtained compound was a transparent liquid, and it was verified by $^1$H-NMR that a SiH group derived from 1,3,5,7-tetrahydrogen-1,3,5,7-tetramethylcyclotetrasiloxane was introduced therein.

2.27 g of a linear polydimethylsiloxane containing vinyl groups at the both ends (produced by Clariant Japan K.K., trade name: MVD8MV) was added to 1.5 g of the compound VIII to give a polyhedral polysiloxane composition as a homogeneous solution. The polysiloxane composition thus obtained was poured into a mold, and cured by heating at 60° C. for 1 hour, at 80° C. for 1 hour, at 100° C. for 1 hour, at 120° C. for 1 hour, at 150° C. for 1 hour, and at 180° C. for 1 hour to give a 3 mm-thick molded product for evaluation. The molded product thus obtained was evaluated for light transmittance. The obtained composition was subjected to an adhesion test. Table 5 shows the results.

TABLE 5

| | Adhesion test | Light transmittance (%) | | | | | |
|---|---|---|---|---|---|---|---|
| | | Initial value | | After heat resistance test | | After light resistance test | |
| | (kgf) | 700 nm | 400 nm | 700 nm | 400 nm | 700 nm | 400 nm |
| Example 37 | 1.6 | 92 | 92 | 92 | 90 | 92 | 90 |
| Reference Example 2 | 0.1 | 92 | 91 | 92 | 91 | 91 | 91 |

As described above, the modified polyhedral polysiloxane of the present invention can be a transparent liquid, and is easily handled in a transparent liquid state. The molded product obtained from the composition with the modified polyhedral polysiloxane exhibits a small decrease in heat and light resistances, and is excellent in adhesiveness to a substrate and in light transmittance.

The invention claimed is:

1. A modified polyhedral polysiloxane, comprising a constitutional unit represented by the formula:

[WR$^3$$_2$SiOSiO$_{3/2}$]$_a$[XR$^5$$_2$SiOSiO$_{3/2}$]$_b$[R$^4$$_3$SiOSiO$_{3/2}$]$_c$ wherein
a+b+c is an integer of 6 to 24, a is an integer of 1 or more, and b and c are each 0 or an integer of 1 or more;
R$^3$ and R$^5$ are each an alkyl group or an aryl group;
R$^4$ is a substituent group other than an alkenyl group and a hydrogen atom;

W is a group having a structure represented by the following formula (3) or (4), wherein in the case where there are a plurality of Ws, the structures of the formula (3) or (4) may be different from each other, or the structures of the formulas (3) and (4) may coexist; and X is a group having a structure represented by the following formula (5) or (6), wherein in the case where there are a plurality of Xs, the structures of the formula (5) or (6) may be different from each other, or the structures of the formulas (5) and (6) may coexist,

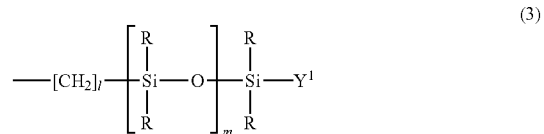
(3)

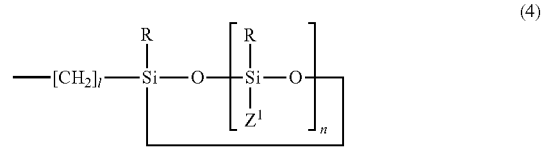
(4)

wherein
l is an integer of 2 or more;
m is an integer of 0 or more;
n is an integer of 2 or more;
R is an alkyl group or an aryl group;
Y$^1$ is an epoxy group-containing group, a hydrogen atom, an alkenyl group, an alkyl group, or an aryl group, and the Y$^1$s may be the same as or different from each other; and
Z$^1$ is an epoxy group-containing group, a hydrogen atom, an alkenyl group, an alkyl group, or an aryl group, and the Z$^1$s may be the same as or different from each other, provided that at least one of the Y$^1$s and Z$^1$s is an epoxy group-containing group,

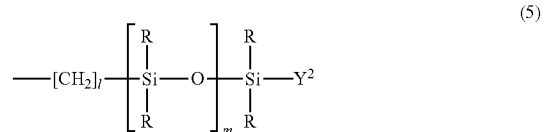
(5)

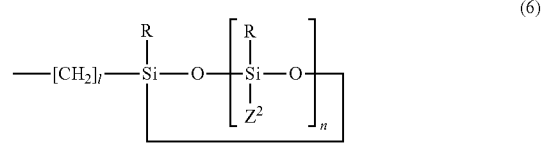
(6)

wherein l is an integer of 2 or more;

m is an integer of 0 or more;

n is an integer of 2 or more;

R is an alkyl group or an aryl group;

$Y^2$ is a hydrogen atom, an alkenyl group, an alkyl group, or an aryl group, and the $Y^2$s may be the same as or different from each other; and $Z^2$ is a hydrogen atom, an alkenyl group, an alkyl group, or an aryl group, and the $Z^2$s may be the same as or different from each other, provided that at least one of the $Y^2$s and $Z^2$s is a hydrogen atom.

2. A polysiloxane composition, comprising:

the modified polyhedral polysiloxane according to claim 1; and a curing initiator.

3. The polysiloxane composition according to claim 2, wherein the curing initiator is a photo-curing initiator.

4. The polysiloxane composition according to claim 3, wherein the photo-curing initiator is an onium salt.

5. The polysiloxane composition according to claim 2, further comprising a hydrosilylation catalyst.

6. The polysiloxane composition according to claim 2, further comprising a curing retardant.

7. The polysiloxane composition according to claim 2, further comprising an adhesion promoter.

8. The polysiloxane composition according to claim 7, wherein the adhesion promoter is a silane coupling agent.

9. The polysiloxane composition according to claim 8, wherein the adhesion promoter is a silane coupling agent containing, in the molecule, a hydrolyzable silyl group and at least one functional group selected from the group consisting of an epoxy group, a methacryl group, an acryl group, an isocyanate group, an isocyanurate group, a vinyl group, and a carbamate group.

10. The polysiloxane composition according to claim 2, further comprising an inorganic filler.

11. A cured product, which is obtained by curing the polysiloxane composition according to claim 2.

12. An encapsulant for optical elements, which is prepared using the polysiloxane composition according to claim 2.

13. A composition for optical elements, which is prepared using the polysiloxane composition according to claim 2.

14. An insulator, which is prepared using the polysiloxane composition according to claim 2.

15. A polysiloxane composition, comprising:

the modified polyhedral polysiloxane according to claim 1; and a curing agent.

16. The polysiloxane composition according to claim 15, wherein the modified polyhedral polysiloxane is the modified polyhedral polysiloxane obtained by modifying the alkenyl group-containing polyhedral polysiloxane compound (a) with the hydrosilyl group-containing compound (b), and the curing agent comprises an alkenyl group-containing polysiloxane with a molecular weight less than 3000 and an alkenyl group-containing polysiloxane with a molecular weight of 5000 or more.

17. The polysiloxane composition according to claim 15, further comprising a hydrosilylation catalyst.

18. The polysiloxane composition according to claim 15, further comprising a curing retardant.

19. The polysiloxane composition according to claim 15, further comprising an adhesion promoter.

20. The polysiloxane composition according to claim 19, wherein the adhesion promoter is a silane coupling agent.

21. The polysiloxane composition according to claim 20, wherein the adhesion promoter is a silane coupling agent containing, in the molecule, a hydrolyzable silyl group and at least one functional group selected from the group consisting of an epoxy group, a methacryl group, an acryl group, an isocyanate group, an isocyanurate group, a vinyl group, and a carbamate group.

22. The polysiloxane composition according to claim 15, further comprising an inorganic filler.

23. A cured product, which is obtained by curing the polysiloxane composition according to claim 15.

24. An encapsulant for optical elements, which is prepared using the polysiloxane composition according to claim 15.

25. A composition for optical elements, which is prepared using the polysiloxane composition according to claim 15.

26. An insulator, which is prepared using the polysiloxane composition according to claim 15.

27. An encapsulant for optical elements, comprising the modified polyhedral polysiloxane according to claim 1.

28. A composition for optical elements, comprising the modified polyhedral polysiloxane according to claim 1.

29. An insulator, comprising the modified polyhedral polysiloxane according to claim 1.

30. The modified polyhedral polysiloxane according to claim 1, wherein $R^4$ is a substituent group other than an alkenyl group and a hydrogen atom that is selected from the group consisting of an alkyl group, an aryl group, and a group bonded to another polyhedral polysiloxane or siloxane compound.

* * * * *